(12) United States Patent
Boyle et al.

(10) Patent No.: US 10,188,342 B2
(45) Date of Patent: Jan. 29, 2019

(54) METHODS, APPARATUSES AND SYSTEMS FOR TRANSCRANIAL STIMULATION

(71) Applicant: The University of North Carolina at Chapel Hill, Chapel Hill, NC (US)

(72) Inventors: Michael R. Boyle, Carrboro, NC (US); Flavio Frohlich, Chapel Hill, NC (US)

(73) Assignee: THE UNIVERSITY OF NORTH CAROLINA AT CHAPEL HILL, Chapel Hill, NC (US)

( * ) Notice: Subject to any disclaimer, the term of this patent is extended or adjusted under 35 U.S.C. 154(b) by 0 days.

(21) Appl. No.: 15/032,155

(22) PCT Filed: Nov. 4, 2014

(86) PCT No.: PCT/US2014/063843
§ 371 (c)(1),
(2) Date: Apr. 26, 2016

(87) PCT Pub. No.: WO2015/069632
PCT Pub. Date: May 14, 2015

(65) Prior Publication Data
US 2016/0256105 A1    Sep. 8, 2016

Related U.S. Application Data

(60) Provisional application No. 61/899,954, filed on Nov. 5, 2013.

(51) Int. Cl.
*A61N 1/04*    (2006.01)
*A61B 5/0476*    (2006.01)
(Continued)

(52) U.S. Cl.
CPC ............ *A61B 5/4836* (2013.01); *A61B 3/112* (2013.01); *A61B 5/0075* (2013.01);
(Continued)

(58) Field of Classification Search
CPC ........ A61N 1/04; A61N 1/32; A61N 1/36021; A61B 5/0476; A61B 5/048; A61B 5/165;
(Continued)

(56) References Cited

U.S. PATENT DOCUMENTS

2002/0169485 A1    11/2002 Pless et al.
2008/0319505 A1    12/2008 Boyden et al.
(Continued)

FOREIGN PATENT DOCUMENTS

RU    39494 U1    8/2004

OTHER PUBLICATIONS

Notification of Transmittal of the International Search Report and the Written Opinion of the International Searching Authority, or Declaration for PCT/US2014/063843 dated Mar. 19, 2015.
(Continued)

*Primary Examiner* — Carl H Layno
*Assistant Examiner* — Jon Eric C Morales
(74) *Attorney, Agent, or Firm* — J. Clinton Wimbish; Nexsen Pruet, PLLC

(57) ABSTRACT

The present invention provides methods, devices and systems for transcranial stimulation.

4 Claims, 9 Drawing Sheets

(51) Int. Cl.
  *A61B 5/00*     (2006.01)
  *A61M 21/00*    (2006.01)
  *A61B 3/11*     (2006.01)
  *A61B 5/0402*   (2006.01)
  *A61B 5/048*    (2006.01)
  *A61B 5/053*    (2006.01)
  *A61N 1/36*     (2006.01)
  *A61N 1/20*     (2006.01)
  *A61B 5/0205*   (2006.01)

(52) U.S. Cl.
  CPC ............ *A61B 5/0402* (2013.01); *A61B 5/048* (2013.01); *A61B 5/0476* (2013.01); *A61B 5/0531* (2013.01); *A61M 21/00* (2013.01); *A61N 1/0484* (2013.01); *A61N 1/20* (2013.01); *A61N 1/36014* (2013.01); *A61N 1/36025* (2013.01); *A61N 1/36031* (2017.08); *A61N 1/36064* (2013.01); *A61N 1/36067* (2013.01); *A61N 1/36071* (2013.01); *A61N 1/36078* (2013.01); *A61N 1/36082* (2013.01); *A61N 1/36085* (2013.01); *A61N 1/36089* (2013.01); *A61N 1/36096* (2013.01); *A61N 1/36139* (2013.01); *A61B 5/0205* (2013.01); *A61M 2021/0072* (2013.01); *A61N 1/0456* (2013.01); *A61N 1/0476* (2013.01)

(58) Field of Classification Search
  CPC .... A61B 5/4094; A61B 5/4812; A61B 5/6814
  USPC .................................... 607/45; 600/411, 544
  See application file for complete search history.

(56) References Cited

U.S. PATENT DOCUMENTS

| | | |
|---|---|---|
| 2009/0112278 A1 | 4/2009 | Wingeier et al. |
| 2009/0299126 A1 | 12/2009 | Fowler et al. |
| 2010/0036453 A1 | 2/2010 | Hulvershorn et al. |
| 2011/0288610 A1 | 11/2011 | Brocke |
| 2013/0295016 A1* | 11/2013 | Gerber .................... A61B 5/16 424/9.2 |

OTHER PUBLICATIONS

Supplemental European Search Report issued in corresponding European Application No. 14860595.9, dated Nov. 14, 2017.

* cited by examiner

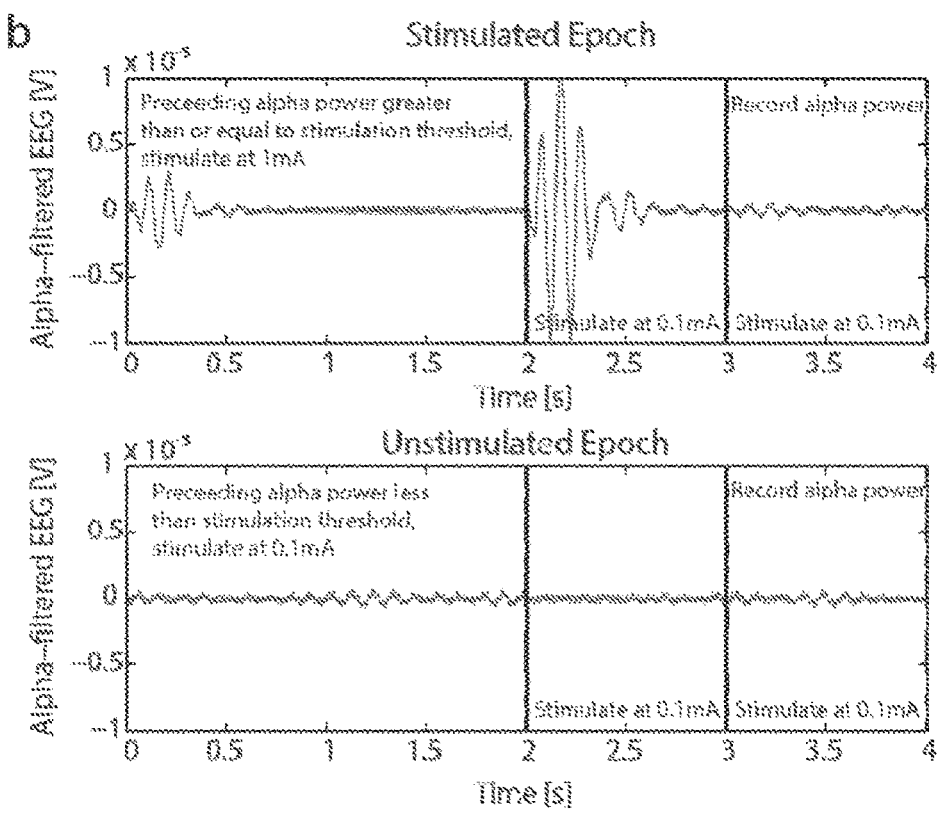
FIG. 1 (contd)

METHODS, APPARATUSES AND SYSTEMS FOR TRANSCRANIAL STIMULATION

STATEMENT OF PRIORITY

This application is a 35 U.S.C. § 371 national phase application of PCT Application PCT/US2014/063843, filed Nov. 4, 2014 which claims the benefit of U.S. Provisional Application Ser. No, 61/899,954, filed Nov. 5, 2013, the entire contents of each of which are incorporated by reference herein.

FIELD OF THE INVENTION

The present invention concerns methods, apparatuses and systems useful for transcranial stimulation.

BACKGROUND

Brain stimulation has gained momentum as an alternative to pharmacological approaches for the treatment of neurological disorders. Although direct targeting of aberrant network dynamics in the brain with electric stimulation offers the opportunity to deliver individualized stimulation with potentially higher efficacy and less undesired side-effects, most of the currently studied stimulation approaches are feedforward systems where the stimulation waveform is preprogrammed.

A need exists for a system that provides better control of dynamics in the cerebral cortex.

SUMMARY OF EMBODIMENTS OF THE INVENTION

The present invention relates to methods, apparatuses and systems that apply stimulation that adapts to simultaneously recorded brain activity, thereby providing better control of activity in the cerebral cortex.

Thus, one aspect of the invention relates to a method of modulating cortical activity in a subject, comprising detecting cortical oscillations and/or coherence between cortical oscillations in the subject and passing an oscillating electric current (OEC) through the skull of the subject responsive to the cortical oscillations and/or coherence detected.

Another aspect of the invention relates to a method of increasing alertness and/or awareness in a subject, comprising passing an oscillating electric current through the skull of the subject.

A further aspect of the invention relates to a method of enhancing one or more cognitive traits in a subject, comprising passing an oscillating electric current through the skull of the subject.

An additional aspect of the invention relates to a method of increasing creativity in a subject, comprising passing an oscillating electric current through the skull of the subject.

Another aspect of the invention relates to a method of preventing and/or treating a neurological disorder in a subject in need thereof, comprising passing an oscillating electric current through the skull of the subject.

A further aspect of the invention relates to a cortical stimulation device, comprising: a detection module configured to detect cortical oscillations in a subject; an analysis module configured to analyze the detected cortical oscillations; a generation module configured to generate an oscillating electric current; and an OEC passing module configured to pass oscillating electric current through the skull of the subject.

An additional aspect of the invention relates to a cortical stimulation device, comprising: a generation module configured to generate an oscillating electric current; and an OEC passing module configured to pass oscillating electric current through the skull of the subject.

DETAILED DESCRIPTION OF THE INVENTION

Figure 1:
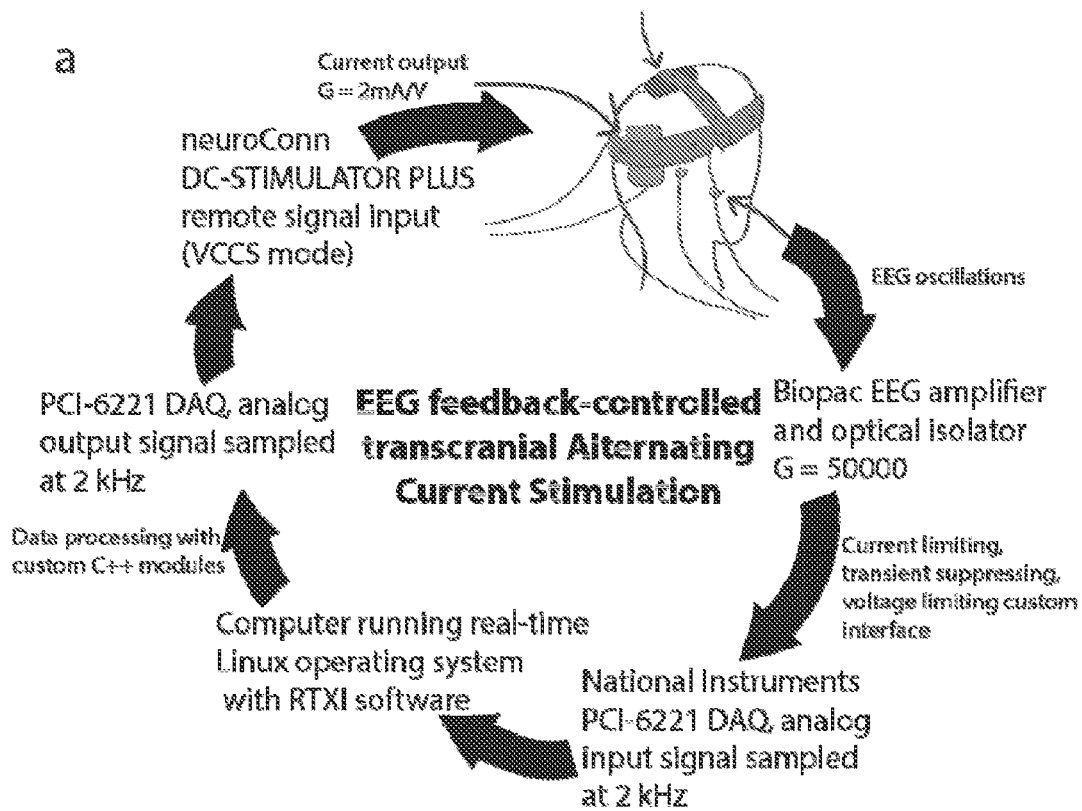
FIG. 1A is a flow chart representing the components of the FB tACS system and methods described in Example 1. The hardware included an EEG amplifier, a desktop computer with a PCI DAQ, and an isolated VCCS. The computer ran a real-time Linux operating system, the RTXI software package, and custom C++ modules that performed the real-time data processing and stimulation waveform generation.
FIG. 1B shows exemplary alpha-filtered EEG traces with 1 mA and 0.1 mA FB tACS. The average alpha power measured in the last 1 s window of each epoch is compared to the stimulation threshold to determine tACS amplitude during the first 2 s of the subsequent epoch. Stimulation amplitude is always 0.1 mA for the last 2 s of each epoch.

The present invention is explained in greater detail below. This description is not intended to be a detailed catalog of all the different ways in which the invention may be implemented or of all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein, which do not depart from the instant invention, will be apparent to those skilled in the art in light of the instant disclosure. Hence, the following specification is intended to illustrate some particular embodiments of the invention, and not to exhaustively specify all permutations, combinations and variations thereof.

It will be understood that when an element or layer is referred to as being "on", "attached to", "connected to", "coupled to", "coupled with" or "contacting" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. It will also be appreciated by those of skill in the art that references to a structure or feature that is disposed "adjacent" another structure or feature may have portions that overlap or underlie the adjacent structure or feature.

The present invention is described below with reference to block diagrams and/or flowchart illustrations of methods, systems and/or computer program products according to embodiments of the invention.

It is understood that various blocks of the block diagrams and/or flowchart illustrations, and combinations of blocks in the block diagrams and/or flowchart illustrations, can be implemented by computer program instructions. These computer program instructions may be provided to a processor of a general purpose computer, special purpose computer and/or other programmable data processing apparatus to produce a machine, such that the instructions, which execute via the processor of the computer or other programmable data processing apparatus, create means for implementing the functions/acts specified in the block diagrams and/or flowchart illustrations. The computer program instructions may also be stored in a computer-readable memory that can direct a computer or other programmable data processing apparatus to function in a particular manner, such that the instructions stored in the computer-readable memory produce an article of manufacture including instructions which implement the function/act specified in the block diagram and/or flowchart illustrations. The computer program instructions may also be loaded onto a computer or other programmable data processing apparatus to cause a series of operational steps to be performed on the computer or other programmable data processing apparatus to produce a computer-implemented process such that the instructions which execute on the computer or other programmable data processing apparatus provide steps for implementing the functions/acts specified in the block diagrams and/or flowchart illustrations.

The flowchart and block diagrams in the figures illustrate the architecture, functionality, and operation of possible implementations of devices, systems, methods and computer program products according to various aspects of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As will be appreciated by one skilled in the art, aspects of the present invention may be embodied in hardware and/or software (including firmware, resident software, microcode, etc.). Accordingly, aspects of the present invention may be illustrated and described herein with respect to various combinations of hardware/software referred to as circuits, modules, devices and/or systems. In some embodiments, aspects of the present invention may take the form of a computer program product on a computer-usable or computer-readable medium having computer-usable or computer-readable program code embodied therein.

Any suitable computer-usable or computer-readable media may be used, including, but not limited to, computer-usable or computer-readable media signal media and computer-usable or computer-readable storage media.

In some embodiments, aspects of the present invention take the form of a computer program product on a computer-usable or computer-readable storage medium (e.g., a non-transient computer-usable or computer-readable storage medium) having computer-usable or computer-readable program code embodied in the medium for use by or in connection with an instruction execution system. A computer-usable or computer-readable storage medium may be any tangible medium that can contain and/or store the program for use by or in connection with the instruction execution system, apparatus or device. For example, the computer-usable or computer-readable storage medium may be an electronic, optical, electromagnetic, infrared or semiconductor system, apparatus or device or any suitable combination thereof. Accordingly, in some embodiments, aspects of the present invention are embodied in portable computer diskette, a hard disk, a random access memory (RAM), a read-only memory (ROM), an erasable programmable read-only memory (EPROM or Flash memory), an optical fiber with a repeater, a portable compact disc read-only memory (CD-ROM), an optical storage device, a magnetic storage device or any suitable combination thereof.

In some embodiments, aspects of the present invention take the form of a computer program product on a computer-usable or computer-readable signal medium having computer-usable or computer-readable program code embodied in the medium for use by or in connection with an instruction execution system. A computer-usable or computer-readable signal medium may be any computer-usable or computer-readable medium that is not a computer-usable or computer-readable storage medium and that can communicate, propagate and/or transport a program for use by or in connection with the instruction execution system, apparatus or device. A computer-usable or computer-readable signal medium may comprise a propagated data signal with computer-usable or computer-readable program code embodied therein. For example, the computer-usable or computer-readable signal medium may comprise computer-usable or computer-readable program code embodied in a baseband or carrier wave. The propagated data signal may take any suitable form, including, but not limited to electro-magnetic and optical. The propagated data signal may be communicated, propagated and/or transmitted using any suitable medium, including, but not limited to, wired and wireless communications channels. Accordingly, in some embodiments, aspects of the present invention are embodied in a computer-usable or computer-readable signal medium that is transmitted over a LAN, the Internet, a public telephone switching network, Bluetooth, WLAN or any suitable combination thereof.

Computer program code for carrying out operations for aspects of the present invention may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer (e.g., entirely on an evaluation portal), partly on the user's computer (e.g., partly on an evaluation portal), as a stand-alone software package, partly on the user's computer and partly on a remote computer (e.g., partly on an evaluation portal and partly on an evaluation hub) or entirely on the remote computer or server (e.g., entirely on an evaluation hub). In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

The terminology used herein is for the purpose of describing particular embodiments only and is not intended to be limiting of the invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

As used herein, the singular forms "a", "an" and "the" are intended to include the plural forms as well, unless the context clearly indicates otherwise.

As used herein, the term "about," when used in reference to a measurable value such as an amount of mass, dose, time, temperature, and the like, is meant to encompass variations of 20%, 10%, 5%, 1%, 0.5%, or even 0.1% of the specified amount.

As used herein, the term "adjuvant treatment" refers to a treatment session/regimen in which the administration of one or more oscillating electric currents (OECs) through the skull of a subject modifies the effect(s) of one or more active agents and/or therapies. For example, the administration of one or more OECs through the skull of a subject may enhance the effectiveness of a pharmaceutical agent (by restoring the therapeutic efficacy of a drug to which the subject had previously become habituated, for example). Likewise, the administration of one or more OECs through the skull of a subject may enhance the effectiveness of counseling or psychotherapy. In some embodiments, the administration of one or more OECs through the skull of a subject reduces or eliminates the need for one or more active agents and/or therapies. Adjuvant treatments may be effectuated by administering one or more OECs through the skull of a subject prior to, currently with and/or after administration of one or more active agents and/or therapies.

As used herein, the term "and/or" includes any and all combinations of one or more of the associated listed items.

As used herein, the terms "chronic treatment," "chronically treating" and the like refer to a therapeutic treatment carried out at least once per week (e.g., two or three times per week, daily, etc.) over an extended period of time. Chronic treatment typically lasts at least one to two weeks (and, in some embodiments, at least one to two months), but may last as long as required to achieve and/or maintain therapeutic efficacy for the particular condition or disorder for which the treatment is carried out (i.e., the device may be used periodically throughout the subject's life).

As used herein, the terms "comprise," "comprises," "comprising," "include," "includes" and "including" specify the presence of stated features, integers, steps, operations, elements, and/or components, but do not preclude the presence or addition of one or more other features, integers, steps, operations, elements, components, and/or groups thereof.

As used herein, the term "consists essentially of" (and grammatical variants thereof), as applied to the compositions and methods of the present invention, means that the compositions/methods may contain additional components so long as the additional components do not materially alter the composition/method. The term "materially alter," as applied to a composition/method, refers to an increase or decrease in the effectiveness of the composition/method of at least about 20% or more. For example, a component added to a composition of the present invention would "materially alter" the composition if it increases or decreases the composition's durability by at least 20%.

As used herein, the term "cortical oscillations" refers to rhythmic and/or repetitive neural activity in the cerebral cortex of a subject. Cortical oscillations may manifest as oscillations in the membrane potential of one or more neurons and/or as the rhythmic firing or one or more neurons. In some embodiments, cortical oscillations arise from and are indicative of synchronized neuronal activity within a specific brain region. In some embodiments, cortical oscillations arise from and are indicative of synchronized neuronal activity in two or more brain regions. In some embodiments, cortical oscillations arise from and are indicative of a feedback loop (e.g., a positive feedback loop) between brain regions. For example, cortical oscillations in the alpha frequency band may arise from and be indicative of a feedback loop in the thalamocortical network.

As used herein, the term "data associated with the administration of one or more OECs" refers to information associated with the administration of one or more OECs and may include, but is not limited to, data associated with cortical oscillations at various time points before, during and/or after administration of the OEC(s); the target parameters of the OEC(s) administered; the parameters of the OEC(s) administered; the date/time each OEC was to be administered; the date/time each OEC was actually administered; reaction time (i.e., how long it took for the subject to react to the OEC(s)); the effectiveness of the OEC(s) (e.g., whether and to what extent symptoms were relieved, whether the OEC(s) enhanced the effectiveness of another agent/therapy, etc.); stability of the treatment (i.e., how long the effects of the treatment lasted); instability of the treatment (i.e., which condition(s) and/or symptom(s) returned and when did it/they return); the presence or absence of comorbid disorders, injuries and/or diseases; disorder, injury and/or disease modulation(s) and/or other modification(s) that occurred as a result of treatment; compliance (e.g., whether the subject initiated administration of the OEC(s) at the prescribed time, whether the subject completed the prescribed treatment session/regimen, whether the device used to administer the OEC(s) (e.g., a cortical stimulation device of the present invention) remained properly fitted on the subject's head for the duration of the treatment session, etc.); the mood of the subject before, during and/or after his/her treatment session(s); objectives measures of efficacy (e.g., electroencephalogram (EEG) data, magnetic resonance imaging (MRI) data, heart rate data, blood pressure data); subjective measures of efficacy (e.g., subject-reported efficacy scores); blood chemistry data; saliva chemistry data; urine chemistry data and comments the subject made about his/her treatment session(s) (e.g., comments made to a physician, submitted in response to an automated survey and/or recorded in a treatment diary). In some embodiments, data associated with the administration of one or more OECs comprises subject feedback data and/or physician feedback data.

As used herein, the terms "enhance" and "increase" (and grammatical variants thereof) refer to an increase in the specified parameter of at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 250%, 300% or more.

As used herein, the terms "inhibit" and "decrease" (and grammatical variants thereof) refer to a decrease in the specified parameter of at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 99% or more.

As used herein, the terms "oscillating electric current" and "OEC" refer to an electric current that periodically reverses polarity.

As used herein, the term "neurological disorder" refers to a disorder of the nervous system. In some embodiments, the neurological disorder is a psychiatric disorder.

As used herein, the term "subject" refers to both human subjects and animal subjects, including, but not limited to, mice, rats, rabbits, cats, dogs, pigs, horses, monkeys, apes, etc. The subject may be male or female. The subject may be of any suitable age, including infant, juvenile, adolescent, adult and geriatric ages. In some embodiments, the methods, devices and systems of the present invention may be used to induce physiological and/or psychological responses in a subject for medically diagnostic and/or therapeutic purposes. For example, the methods, devices and systems of the present invention may be used to diagnose and/or treat mammalian subjects, such as mice, rats, pigs and monkeys, for medical research or veterinary purposes.

As used herein, the term "subject feedback data" refers to data associated with subject feedback regarding the administration of one or more OECs. Subject feedback data may comprise, but is not limited to, a subject's evaluation of their symptom(s) before, during and/or after administration of the OEC(s) and subject comments (e.g., comments regarding a subject's opinion as to the efficacy of a treatment session/regimen or the effect(s) of certain treatment modifications, etc.).

As used herein, the term "physician feedback data" refers to data associated with physician feedback regarding the administration of one or more OECs. Physician feedback data may comprise, but is not limited to, comments from one or more physicians (e.g., comments regarding a physician's opinion as to the efficacy of a given treatment session/regimen or the effect(s) of certain treatment modifications, etc.).

As used herein, the terms "prevent," "preventing," and "prevention" (and grammatical variants thereof) refer to avoiding the onset of a disorder and/or a clinical symptom(s) in a subject relative to what would occur in the absence of the methods of the present invention. In some embodiments, prevention is complete, resulting in the total absence of the disorder and/or clinical symptom(s) (e.g., a total absence of growth of a pathogenic microbial strain). In some embodiments, prevention is partial, resulting in avoidance of some aspects of the disorder and/or clinical symptom(s) (e.g., prevention of positive symptoms (e.g., hallucinations) but not negative symptoms (e.g., flat affect)).

As used herein, the term "prevention effective amount" (and grammatical variants thereof) refers an amount that is sufficient to prevent and/or delay the onset of a disorder and/or clinical symptoms in a subject and/or to reduce and/or delay the severity of the onset of a disorder and/or clinical symptoms in a subject relative to what would occur in the absence of the methods of the invention. Those skilled in the art will appreciate that the level of prevention need not be complete, as long as some benefit is provided to the subject.

As used herein, the terms "therapeutically effective amount" and "therapeutically acceptable amount" (and grammatical variants thereof) refer to an amount that will elicit a therapeutically useful response in a subject. The therapeutically useful response may provide some alleviation, mitigation, or decrease in at least one clinical symptom in the subject. The terms also include an amount that will prevent and/or delay the onset of at least one clinical symptom in the subject and/or reduce and/or delay the severity of the onset of a clinical symptom in a subject relative to what would occur in the absence of the methods of the invention. Those skilled in the art will appreciate that the therapeutically useful response need not be complete or curative or prevent permanently, as long as some benefit is provided to the subject.

As used herein, the terms "treat," "treatment" and "treating" refer to reversing, alleviating, reducing the severity of and/or inhibiting the progress of a disease or disorder as described herein, or at least one symptom of a disease or disorder as described herein (e.g., treating tremors, bradykinesia, rigidity or postural instability associated with Parkinson's disease; treating hallucinations or delusions associate with schizophrenia; treating intrusive thoughts such as intrusive emotions, intrusive memories, nightmares and night terrors; treating hyperarousal symptoms such as exaggerated startle reactions, explosive outbursts, extreme vigilance, irritability, panic symptoms, sleep disturbances; treating tinnitus). In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved—for example, to prevent or delay their recurrence. Treatment may be as an adjuvant treatment as further described herein.

As used herein, the term "treatment effective amount" (and grammatical variants thereof) refers to an amount that is sufficient to provide some improvement or benefit to the subject. Alternatively stated, a "treatment effective amount" is an amount that will provide some alleviation, mitigation, decrease, or stabilization in at least one clinical symptom in the subject. Those skilled in the art will appreciate that the therapeutic effects need not be complete or curative, as long as some benefit is provided to the subject.

All publications, patent applications, patents, and other references mentioned herein are incorporated by reference in their entirety.

Methods

The present invention provides methods of modulating cortical activity, methods of modulating cortical states, methods of enhancing one or more cognitive traits, methods of enhancing creativity, and methods of treating one or more neurological disorders. In some embodiments, methods of the present invention comprise, consist essentially of or consist of passing one or more OECs through the skull of a subject (e.g., a patient). In some embodiments, methods of the present invention comprise, consist essentially of or consist of detecting cortical oscillations and/or coherence between cortical oscillations (e.g., coherence between cortical oscillations of a specific frequency (or group of frequencies)) in a subject and passing one or more OECs through the skull of the subject responsive to the cortical oscillations and/or coherence detected.

Any suitable OEC may be passed through the skull of a subject, including, but not limited to, oscillations in the delta frequency band (1-4 Hz), oscillations in the theta frequency band (4-8 Hz), oscillations in the alpha frequency band (8-13 Hz), oscillations in the beta frequency band (13-30 Hz) and oscillations in the gamma frequency band (30-70 Hz). In some embodiments, the magnitude(s) of the OEC(s) is/are sufficient to prevent cortical oscillations in a subject's brain (e.g., cortical oscillations in the alpha frequency band) from exceeding an upper threshold, to prevent cortical oscillations in a subject's brain (e.g., cortical oscillations in the gamma frequency band) from falling below a lower threshold, to increase the synchronization of cortical oscillations within a first brain region of a subject's brain, to increase the synchronization of cortical oscillations in a first region of a subject's brain with cortical oscillations in a second region of the subject's brain, to decrease the synchronization of cortical oscillations within a first region of a subject's brain and/or to decrease the synchronization of cortical oscillations in a first region of a subject's brain with cortical oscillations in a second region of the subject's brain. In some embodiments, the magnitude(s) of the OEC(s) is/are proportional to one or more characteristics of the cortical oscillations detected in one or more regions of a subject's brain. For example, the magnitude of OECs in the gamma frequency band may be proportional to the magnitude cortical oscillations in the alpha frequency band and may be sufficient to prevent the magnitude of cortical oscillations in the alpha frequency band from exceeding an upper threshold.

One or more characteristics of the OEC(s) may be modulated in response to changes in cortical oscillations in the subject's brain. In some embodiments, one or more characteristics of the OEC(s) is be modulated in response to a change in the magnitude, frequency and/or coherence of cortical oscillations in the subject's brain. In some embodiments, the OEC(s) is/are modulated in real time responsive to analysis of the cortical oscillations.

Any suitable characteristic of the OEC(s) may be modulated in response to changes in cortical oscillations in the subject's brain, including, but not limited to, the magnitude, frequency and/or duration of each OEC.

OECs may be passed through the skull of a subject using any suitable method/apparatus, including, but not limited to, pairs of electrodes. In some embodiments, the OEC(s) are passed through the skull of the subject using one or more pairs of electrodes placed (either directly or indirectly) in contact with the scalp of the subject. Electrodes may be placed at any suitable position(s) on the scalp, including, but not limited to, the positions defined by the International 10-20 System of Electrode Placement.

OECs may be passed through the skull of a subject into any suitable region(s) of the subject's brain, including, but not limited to, the subject's occipital lobe, parietal lobe, temporal lobe, frontal lobe, visual cortex, auditory cortex, somatosensory cortex, premotor cortex, motor cortex, prefrontal cortex, Wernicke's area, Broca's area, sensory association area, auditory association area and/or visual association area. In some embodiments, OECs are passed through the skull of a subject into two or more regions of the subject's brain concurrently. In some embodiments, OECs are passed through the skull of a subject into two or more regions of the subject's brain sequentially. For example, cortical oscillations may be concurrently/sequentially passed through the skull of a subject into the auditory cortex, the prefrontal cortex and/or temporoparietal cortex of the subject's brain (to treat schizophrenia, for example). In some embodiments, OECs are passed concurrently/sequentially through the skull of a subject into premotor cortex and/or primary motor cortex (to treat a movement disorder, for example).

Cortical oscillations and/or coherence may be detected using any suitable device/system/method. In some embodiments, cortical oscillations and/or coherence are detected using an electroencephalogram, an electrocardiogram, a pupilometer and/or a functional near-infrared spectrometer. In some embodiments, cortical oscillations and/or coherence are detected by identifying one or more changes in the subject's pupil diameter, the subject's skin conductance, the subject's heart rate and/or the regularity of the subject's heartbeat.

Cortical oscillations and/or coherence may be detected in any suitable region(s) of a subject's brain, including, but not limited to, the subject's occipital lobe, parietal lobe, temporal lobe, frontal lobe, visual cortex, auditory cortex, somatosensory cortex, premotor cortex, subject's motor cortex, prefrontal cortex, Wernicke's area, Broca's area, sensory association area, auditory association area and/or visual association area. In some embodiments, cortical oscillations are detected in two or more regions of the subject's brain concurrently. In some embodiments, cortical oscillations are detected in two or more regions of the subject's brain sequentially. For example, cortical oscillations may be concurrently/sequentially detected in the auditory cortex, the prefrontal cortex and/or temporoparietal cortex of the subject's brain (in a subject with schizophrenia, for example). In some embodiments, cortical oscillations are detected concurrently/sequentially in the subject's premotor cortex and/or primary motor cortex (in a subject with a movement disorder, for example).

Any suitable cortical oscillations may be detected, including, but not limited to, oscillations in the delta frequency band (1-4 Hz), oscillations in the theta frequency band (4-8 Hz), oscillations in the alpha frequency band (8-13 Hz), oscillations in the beta frequency band (13-30 Hz) and oscillations in the gamma frequency band (30-70 Hz).

In some embodiments, the cortical oscillations oscillate in the same frequency band(s) as the OECs. For example, both the cortical oscillations and the OECs may oscillate in the alpha frequency band.

In some embodiments, cortical oscillations oscillate in a first frequency band (or group of frequency bands) and the OECs oscillate in a second frequency band (or group of frequency bands). In some such embodiments, the first frequency band (or group of frequency bands) and the second frequency band (or group of frequency bands) are mutually exclusive (i.e., there is no overlap between the two frequency bands). For example, the cortical oscillations may oscillate in the alpha frequency band and the OECs may oscillate in the gamma frequency band. In some such embodiments, the first frequency band (or group of frequency bands) and the second frequency band (or group of frequency bands) partially overlap. For example, the cortical oscillations may oscillate in the theta and alpha frequency bands and the OECs may oscillate in the alpha frequency band.

In some embodiments, cortical oscillations are detected in and the OEC(s) is/are passed into the same region(s) of a subject's brain. For example, cortical oscillations may be detected in and OECs may be passed into the auditory cortex, the prefrontal cortex and/or temporoparietal cortex of the subject's brain (in a subject with schizophrenia, for example).

In some embodiments, cortical oscillations are detected in a first brain region (or group of brain regions) and the OEC(s) is/are passed through the subject's skull into a second brain region (or group of brain regions). In some such embodiments, the first and second brain regions (or groups of brain regions) are mutually exclusive (i.e., there is no overlap between the two regions (or groups of brain regions)). For example, cortical oscillations may be detected in the auditory cortex of the subject's brain and OECs may be passed into the parietal cortex of the subject's brain (in a subject with schizophrenia, for example). In some such embodiments, the first and second brain regions (or groups of brain regions) partially overlap (i.e., some portion(s) of the subject's brain is part of both regions (or groups of brain regions)). For example, cortical oscillations may be detected in the auditory cortex and parietal cortex of the subject's brain and OECs may be passed into the parietal cortex of the subject's brain (in a subject with schizophrenia, for example).

OECs may be generated and passed through the skull of a subject responsive to any suitable stimulus.

In some embodiments, one or more OECs is passed through the skull of the subject responsive to the magnitude of the cortical oscillations, the difference between the magnitude of the cortical oscillations and a target value, whether the magnitude of the cortical oscillations has exceeded an upper threshold, the difference between the magnitude of the cortical oscillations and an upper threshold, whether the magnitude of the cortical oscillations has fallen below a lower threshold and/or the difference between the magnitude of the cortical oscillations and a lower threshold.

In some embodiments, one or more OECs is passed through the skull of the subject responsive to the variance of the magnitude of the cortical oscillations over a defined period of time, the difference between the variance of the magnitude of the cortical oscillations and a target value, whether the variance of the magnitude of the cortical oscillations over a defined period of time has exceeded an upper threshold, the difference between the variance of the magnitude of the cortical oscillations over a defined period of time and an upper threshold, whether the variance of the magnitude of the cortical oscillations over a defined period of time has fallen below a lower threshold and/or the difference between the variance of the magnitude of the cortical oscillations over a defined period of time and a lower threshold.

In some embodiments, one or more OECs is passed through the skull of the subject responsive to the integral of the magnitude of the cortical oscillations, the difference between the integral of the magnitude of the cortical oscillations and a target value, whether the integral of the magnitude of the cortical oscillations over a defined period of time has exceeded an upper threshold, the difference between the integral of the magnitude of the cortical oscillations and an upper threshold, whether the integral of the magnitude of the cortical oscillations over a defined period of time has fallen below a lower threshold and/or the difference between the integral of the magnitude of the cortical oscillations and a lower threshold.

In some embodiments, one or more OECs is passed through the skull of the subject responsive to the temporal derivative of the magnitude of the cortical oscillations, the difference between the temporal derivative of the magnitude of the cortical oscillations and a target value, whether the temporal derivative of the magnitude of the cortical oscillations over a defined period of time has exceeded an upper threshold, the difference between the temporal derivative of the magnitude of the cortical oscillations and an upper threshold, whether the temporal derivative of the magnitude of the cortical oscillations over a defined period of time has fallen below a lower threshold and/or the difference between the temporal derivative of the magnitude of the cortical oscillations and a lower threshold.

In some embodiments, one or more OECs is passed through the skull of the subject responsive to the average magnitude of the cortical oscillations over a defined period of time, the difference between the average magnitude of the cortical oscillations over a defined period of time and a target value, whether the average magnitude of the cortical oscillations over a defined period of time has exceeded an upper threshold, the difference between the average magnitude of the cortical oscillations over a defined period of time and an upper threshold, whether the average magnitude of the cortical oscillations over a defined period of time has fallen below a lower threshold and/or the difference between the average magnitude of the cortical oscillations over a defined period of time and a lower threshold.

In some embodiments, one or more OECs is passed through the skull of the subject responsive to the variance of the average magnitude of the cortical oscillations over a defined period of time, the difference between the variance of the average magnitude of the cortical oscillations over a defined period of time and a target value, whether the variance of the average magnitude of the cortical oscillations over a defined period of time has exceeded an upper threshold, the difference between the variance of the average magnitude of the cortical oscillations over a defined period of time and an upper threshold, whether the variance of the average magnitude of the cortical oscillations over a defined period of time has fallen below a lower threshold and/or the difference between the variance of the average magnitude of the cortical oscillations over a defined period of time and a lower threshold.

In some embodiments, one or more OECs is passed through the skull of the subject responsive to the integral of the average magnitude of the cortical oscillations over a defined period of time, the difference between the integral of the average magnitude of the cortical oscillations over a defined period of time and a target value, whether the integral of the average magnitude of the cortical oscillations over a defined period of time has exceeded an upper threshold, the difference between the integral of the average magnitude of the cortical oscillations over a defined period of time and an upper threshold, whether the integral of the average magnitude of the cortical oscillations over a defined period of time has fallen below a lower threshold and/or the difference between the integral of the average magnitude of the cortical oscillations over a defined period of time and a lower threshold.

In some embodiments, one or more OECs is passed through the skull of the subject responsive to the temporal derivative of the average magnitude of the cortical oscillations over a defined period of time, the difference between the temporal derivative of the average magnitude of the cortical oscillations over a defined period of time and a target value, whether the temporal derivative of the average magnitude of the cortical oscillations over a defined period of time has exceeded an upper threshold, the difference between the temporal derivative of the average magnitude of the cortical oscillations over a defined period of time and an upper threshold, whether the temporal derivative of the average magnitude of the cortical oscillations over a defined period of time has fallen below a lower threshold and/or the difference between the temporal derivative of the average magnitude of the cortical oscillations over a defined period of time and a lower threshold.

In some embodiments, one or more OECs is passed through the skull of the subject responsive to whether the cortical oscillations within a first brain region are synchronized, to what degree the cortical oscillations in a first brain region are synchronized, the difference between the degree of synchronization of the cortical oscillations within a first brain region and a target value, whether the degree of synchronization of the cortical oscillations within a first brain region has exceeded an upper threshold, the difference between the degree of synchronization of the cortical oscillations within a first brain region and an upper threshold, whether the degree of synchronization of the cortical oscillations within a first brain region has fallen below a lower threshold and/or the difference between the degree of synchronization of the cortical oscillations within a first brain region and a lower threshold.

In some embodiments, one or more OECs is passed through the skull of the subject responsive to the variance of the degree of synchronization of the cortical oscillations within a first brain region over a defined period of time, the difference between the variance of the degree of synchronization of the cortical oscillations within a first brain region and a target value, whether the variance of the degree of synchronization of the cortical oscillations within a first brain region has exceeded an upper threshold, the difference between the variance of the degree of synchronization of the cortical oscillations within a first brain region and an upper threshold, whether the variance of the degree of synchronization of the cortical oscillations within a first brain region has fallen below a lower threshold and/or the difference between the variance of the degree of synchronization of the cortical oscillations within a first brain region and a lower threshold.

In some embodiments, one or more OECs is passed through the skull of the subject responsive to the average degree of synchronization of the cortical oscillations within a first brain region over a defined period of time, the difference between the average degree of synchronization of the cortical oscillations within a first brain region and a target value, whether the average degree of synchronization of the cortical oscillations within a first brain region has exceeded an upper threshold, the difference between the average degree of synchronization of the cortical oscillations within a first brain region and an upper threshold, whether the average degree of synchronization of the cortical oscillations within a first brain region has fallen below a lower threshold and/or the difference between the average degree of synchronization of the cortical oscillations within a first brain region and a lower threshold.

In some embodiments, one or more OECs is passed through the skull of the subject responsive to the variance of the average degree of synchronization of the cortical oscillations within a first brain region over a defined period of time, the difference between the variance of the average degree of synchronization of the cortical oscillations within a first brain region and a target value, whether the variance of the average degree of synchronization of the cortical oscillations within a first brain region has exceeded an upper threshold, the difference between the variance of the average degree of synchronization of the cortical oscillations within a first brain region and an upper threshold, whether the variance of the average degree of synchronization of the cortical oscillations within a first brain region has fallen below a lower threshold and/or the difference between the variance of the average degree of synchronization of the cortical oscillations within a first brain region and a lower threshold.

In some embodiments, one or more OECs is passed through the skull of the subject responsive to whether the cortical oscillations in a first brain region are synchronized with the cortical oscillations in a second brain region, to what degree the cortical oscillations in a first brain region are synchronized with the cortical oscillations in a second brain region, the difference between the degree of synchronization between the cortical oscillations in a first brain region and the cortical oscillations in a second brain region and a target value, whether the degree of synchronization between the cortical oscillations in a first brain region and the cortical oscillations in a second brain region has exceeded an upper threshold, the difference between the degree of synchronization between the cortical oscillations in a first brain region and the cortical oscillations in a second brain region and an upper threshold, whether the degree of synchronization of the cortical oscillations between the cortical oscillations in a first brain region and the cortical oscillations in a second brain region has fallen below a lower threshold and/or the difference between the degree of synchronization of the cortical oscillations between the cortical oscillations in a first brain region and the cortical oscillations in a second brain region and a lower threshold.

In some embodiments, one or more OECs is passed through the skull of the subject responsive to the variance of the degree of synchronization of the cortical oscillations between the cortical oscillations in a first brain region and the cortical oscillations in a second brain region over a defined period of time, the difference between the variance of the degree of synchronization of the cortical oscillations between the cortical oscillations in a first brain region and the cortical oscillations in a second brain region and a target value, whether the variance of the degree of synchronization of the cortical oscillations between the cortical oscillations in a first brain region and the cortical oscillations in a second brain region has exceeded an upper threshold, the difference between the variance of the degree of synchronization of the cortical oscillations between the cortical oscillations in a first brain region and the cortical oscillations in a second brain region and an upper threshold, whether the variance of the degree of synchronization of the cortical oscillations between the cortical oscillations in a first brain region and the cortical oscillations in a second brain region has fallen below a lower threshold and/or the difference between the variance of the degree of synchronization of the cortical oscillations between the cortical oscillations in a first brain region and the cortical oscillations in a second brain region and a lower threshold.

In some embodiments, one or more OECs is passed through the skull of the subject responsive to the average degree of synchronization of the cortical oscillations between the cortical oscillations in a first brain region and the cortical oscillations in a second brain region over a defined period of time, the difference between the average degree of synchronization of the cortical oscillations between the cortical oscillations in a first brain region and the cortical oscillations in a second brain region and a target value, whether the average degree of synchronization of the cortical oscillations between the cortical oscillations in a first brain region and the cortical oscillations in a second brain region has exceeded an upper threshold, the difference between the average degree of synchronization of the cortical oscillations between the cortical oscillations in a first brain region and the cortical oscillations in a second brain region and an upper threshold, whether the average degree of synchronization of the cortical oscillations between the cortical oscillations in a first brain region and the cortical oscillations in a second brain region has fallen below a lower threshold and/or the difference between the average degree of synchronization of the cortical oscillations between the cortical oscillations in a first brain region and the cortical oscillations in a second brain region and a lower threshold.

In some embodiments, one or more OECs is passed through the skull of the subject responsive to the variance of the average degree of synchronization of the cortical oscillations between the cortical oscillations in a first brain region and the cortical oscillations in a second brain region over a defined period of time, the difference between the variance of the average degree of synchronization of the cortical oscillations between the cortical oscillations in a first brain region and the cortical oscillations in a second brain region and a target value, whether the variance of the average degree of synchronization of the cortical oscillations between the cortical oscillations in a first brain region and the cortical oscillations in a second brain region has exceeded an upper threshold, the difference between the variance of the average degree of synchronization of the cortical oscillations between the cortical oscillations in a first brain region and the cortical oscillations in a second brain region and an upper threshold, whether the variance of the average degree of synchronization of the cortical oscillations between the cortical oscillations in a first brain region and the cortical oscillations in a second brain region has fallen below a lower threshold and/or the difference between the variance of the average degree of synchronization of the cortical oscillations between the cortical oscillations in a first brain region and the cortical oscillations in a second brain region and a lower threshold.

In some embodiments, one or more OECs is passed through the skull of the subject responsive to a signal generated in response to analysis of cortical oscillations.

OECs may be generated in real time. In some embodiments, one or more OECs is generated in real time responsive to analysis of cortical oscillations.

Methods of the present invention may further comprise administering at least one pharmaceutical agent to the subject. In some embodiments, the at least one pharmaceutical agent is administered prior to passage of the OEC through the skull of the subject. In some embodiments, the at least one pharmaceutical agent is administered concurrently with passage of the OEC through the skull of the subject. In some embodiments, the at least one pharmaceutical agent is administered following passage of the OEC through the skull of the subject. In some embodiments, the at least one pharmaceutical agent comprises a plurality of pharmaceutical agents.

Any suitable pharmaceutical agent may be administered to the subject, including, but not limited to, antidepressants (e.g., selective serotonin reuptake inhibitors (e.g., fluoxetine, paroxetine, citalopram, escitalopram, sertraline), monoamine oxidase inhibitors (e.g., isocarboxazid, phenelzine)), stimulants (e.g., caffeine, methylphenidate, dexmethylphenidate, dextroamphetamine, levoamphetamine, methamphetamine, modafinil), antipsychotics (e.g., risperidone, quetiapine, olanzapine, lurasidone, aripiprazole, asenapine, butyrophenones (e.g., benperidol, droperidol, haloperidol), paliperidone, ziprasidone, clozapine, amisulpride, amoxapine, blonanserin, iloperidone, melperone, perospirone, sertindole, zotepine, perphenazine, phenothiazines (e.g., chlorpromazine, cyamemazine, fluphenazine, levomepromazine, mesoridazine, pericyazine, perphenazine, prochlorperazine, promazine, promethazine, thioridazine, trifluoperazine, triflupromazine), thioxanthenes (e.g., chlorprothixene, clopenthixol, flupenthixol, thiothixene, zuclopenthixol), loxapine, pimozide, sulpiride, trimipramine), mood stabilizers (e.g., lithium, valproate, carbamazepine, oxcarbazepine, lamotrigine, gabapentin, pregabalin, topiramate, olanzapine), anxiolytics, hallucinogens (e.g., LSD, psilocybin, mescaline, ibogaine, cannabis, dimethyltryptamine), hypnotics (e.g., diazepam, nitrazepam, zolpidem, zopiclone, zaleplon, chlordiazepoxide, alprazolam, temazepam, clonazepam, lorazepam), sedatives (e.g., barbiturates (e.g., amobarbital, pentobarbital, secobarbital, phenobarbital), antihistamines (diphenhydramine, dimenhydrinate, doxyamine, mirtazapine, promethazine), herbal sedatives (e.g., cannabis, kava, valerian, validol), chloral hydrate, trazodone, alcohol, opiates, glutethimide), and anesthetics (e.g., desflurane, enflurane, halothane, isoflurane, methoxyflurane, nitrous oxide, sevoflurane, xenon, amobarbital, methohexital, thiamylal, thiopental, etomidate, ketamine, propofol, alfentanil, fentanyl, remifentanil, sufentanil, buprenorphine, butorphanol, hydromorphone, diacetyl morphine, levorphanol, meperidine, methadone, morphine, nalbuphine, oxycodone, oxymorphone, pentazocine, muscle relaxants (e.g., succinylcholine, decamethonium, mivacurium, rapacuronium, atracurium, cisatracium, rocuronium, vecuronium, alcuronium, doxacurium, gallamine, metocurine, pancuronium, pipecuronium, tubocurarine)).

Pharmaceutical agents may be administered to the subject in any suitable amount(s). In some embodiments, each pharmaceutical agent is administered to the subject in a therapeutically effective amount. In some embodiments, each pharmaceutical agent is administered to the subject in an amount that would not be therapeutically effective if not combined with passage of the OEC through the skull of the subject.

Given the teaching provided by the present disclosure and the general knowledge available to those skilled in the art with respect to pharmaceutical agents, those skilled in the art will understand how to select and/or optimize administration of the pharmaceutical agent(s) to achieve a therapeutic effect and/or to enhance the therapeutic effect of the OEC.

Methods of the present invention may further comprise administering one or more psychotherapies to the subject. In some embodiments, the at least one psychotherapy is administered prior to passage of the OEC through the skull of the subject. In some embodiments, at least one psychotherapy is administered concurrently with passage of the OEC through the skull of the subject. In some embodiments, the at least one psychotherapy is administered following passage of the OEC through the skull of the subject.

Any suitable psychotherapy may be administered to the subject, including, but not limited to, art therapy, behavioral modification, behavioral therapies, cognitive analytic therapy, cognitive behavior therapy, coherence therapy, dialectical behavior therapy, existential therapy, family therapy, holistic psychotherapy, hypnotherapy, marriage counseling, multimodal therapy, music therapy, pastoral counseling, play therapy, primal therapy, process-oriented psychology, prolonged exposure therapy, psychoanalysis, relationship counseling, reprogramming, sexual identity therapy, social therapy, systematic desensitization, systemic therapy, transference focused psychology, twelve step programs and wilderness therapy. Psychotherapies may be administered to the subject according to any suitable protocol.

Given the teaching provided by the present disclosure and the general knowledge available to those skilled in the art with respect to psychotherapy, those skilled in the art will understand how to select and/or optimize the administration of the psychotherapy(ies) to achieve a therapeutic effect and/or to enhance the therapeutic effect of the OEC.

Methods of the present invention may modulate cortical activity in any suitable manner, including, but not limited to, inhibiting cortical oscillations (e.g., cortical oscillations in the alpha frequency band), enhancing cortical oscillations (e.g., cortical oscillations in the gamma frequency band), increasing the coherence of cortical oscillations (e.g., increasing the coherence of cortical oscillations within a brain region and/or increasing the coherence of cortical oscillations in a first brain region with cortical oscillations in one or more different brain regions) and decreasing the coherence of cortical oscillations (e.g., decreasing the coherence of cortical oscillations within a brain region and/or decreasing the coherence of cortical oscillations in a first brain region with cortical oscillations in one or more different brain regions). In some embodiments, OECs in the gamma frequency band are used to enhance cortical oscillations in the delta, theta and/or gamma frequency bands, to inhibit cortical oscillations in the alpha and/or beta frequency bands and/or to reduce the variance of cortical oscillations in the delta, theta, alpha, beta and/or gamma frequency bands. In some embodiments, low frequency OECs (e.g., cortical oscillations in the sub-delta and/or delta frequency bands) are used to enhance cortical oscillations in the delta, beta and/or gamma frequency bands and/or to reduce the variance of cortical oscillations in the delta, beta and/or gamma frequency bands. In some embodiments, OECs in the alpha frequency band are used to enhance cortical oscillations in the alpha frequency band, to inhibit cortical oscillations in the gamma frequency band and/or to reduce the variance of cortical oscillations in the alpha and/or gamma frequency bands.

Given the teaching provided by the present disclosure and the general knowledge available to those skilled in the art with respect to cortical states and cortical oscillations, those skilled in the art will understand how to select and/or optimize OECs to achieve the desired effect(s).

Methods of the present invention may be used to prevent and/or treat any suitable neurological disorder, including, but not limited to, aphasias (e.g., receptive aphasias, expressive aphasias, pure alexia), apraxias (e.g., ideomotor apraxia, conceptual apraxia, gait apraxia), agnosias (e.g., akinetopsia, anosognosia, visual agnosia, auditory agnosia, verbal agnosia, asterognosis, phoagnosia, prosopagnosia, alexia, tactile agnosia, time agnosia) and amnesias (e.g., dissociative amnesia, epileptic amnesia). In some embodiments, methods of the present invention are used to treat an anxiety disorder such as social anxiety disorder, obsessive-compulsive disorder, post-traumatic stress disorder, generalized anxiety disorder, situational anxiety, separation anxiety or a phobia (e.g., agoraphobia). In some embodiments, methods of the present invention are used to treat an eating disorder such as anorexia nervosa or bulimia nervosa. In some embodiments, methods of the present invention are used to treat a mood disorder such as a bipolar disorder or a depressive disorder. In some embodiments, methods of the present invention are used to treat a personality disorder such as schizoid, paranoid, schizotypal, antisocial, borderline, histrionic, narcissistic, avoidant, dependent or obsessive-compulsive personality disorder. In some embodiments, methods of the present invention are used to treat a psychotic disorder such as schizophrenia. In some embodiments, methods of the present invention are used to treat a substance use disorder such as substance dependence and substance abuse. In some embodiments, methods of the present invention are used to treat a somatoform disorder such as body dysmorphic disorder, hypochondriasis, pain disorder or conversion disorder. In some embodiments, methods of the present invention are used to treat a developmental disorder such as an autism spectrum disorder (e.g., Asperger syndrome) or attention deficit disorder. In some embodiments, methods of the present invention are used to treat a neurodegenerative disease such as Alzheimer's disease, Parkinson's disease or Huntington's disease. In some embodiments, methods of the present invention are used to treat a seizure disorder such as epilepsy. In some embodiments, methods of the present invention are used to treat a movement disorder such as bradykinesia, chorea (e.g., Huntington's disease), Parkinson's disease, tic disorders (e.g., Tourette's Syndrome), multiple sclerosis, amyotrophic lateral sclerosis, tremors or cerebral palsy. In some embodiments, methods of the present invention are used to treat a sleep disorder such as hypersomnias (e.g., narcolepsy), parasomnias (e.g., sleep terrors, sleep enuresis, somniloquy) or insomnia. In some embodiments, methods of the present invention are used to treat dementia.

Methods of the present invention may be used to prevent and/or treat neurological disorders in any suitable manner, including, but not limited to, inhibiting and/or delaying onset of a disorder/symptom, inhibiting and/or delaying reoccurrence of a disorder/symptom, decreasing the length of time from onset of a disorder/symptom to remission of the disorder/symptom, increasing the amount of time spent in remission, increasing the number of symptom-free days, decreasing the severity of one or more symptoms. In some embodiments, inhibition of the disorder/symptom is complete, resulting in the total absence of the disorder and/or clinical symptom(s) (e.g., a total absence of hallucinations). In some embodiments, inhibition is partial, resulting in reduced severity and/or delayed onset of the disorder and/or clinical symptom(s) (e.g., a reduction in the frequency of hallucinations).

Methods of the present invention may be used to decrease the length of time from onset of a disease/symptom to remission of the disease/symptom by at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 99% or more as compared to a control subject/population (e.g., a subject/population to which the OEC was not administered).

Methods of the present invention may be used to decrease the severity of one or more symptoms of a neurological disorder by at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 99% or more as compared to a control subject/population (e.g., a subject/population to which the OEC was not administered).

Methods of the present invention may be used to increase the amount of time spent in remission from a neurological disorder by at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 250%, 300% or more as compared to a control subject/population (e.g., a subject/population to which the OEC was not administered).

Methods of the present invention may be used to increase the number of symptom-free days by at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 250%, 300% or more as compared to a control subject/population (e.g., a subject/population to which the OEC was not administered).

Methods of the present invention may be used in the chronic treatment of neurological disorders.

Given the teaching provided by the present disclosure and the general knowledge available to those skilled in the art with respect to neurological disorders, those skilled in the art will understand how to select and/or optimize methods of the present invention to prevent and/or treat a given disease/symptom. Table 1 sets forth exemplary combinations of the cortical oscillations that may be detected and the OECs that may be administered in the treatment of neurological disorders.

TABLE 1

Exemplary combinations of the cortical oscillations and OECs used in the treatment of neurological disorders/symptoms.

| Disorder/Symptom to be Treated | Frequency Band of the Cortical Oscillations Detected | Frequency Band of the OECs Administered |
|---|---|---|
| schizophrenia | alpha | gamma |
| schizophrenia | gamma | gamma |
| autism | alpha | gamma |
| autism | gamma | gamma |
| ADHD | alpha | gamma |
| Alzheimer's disease | alpha | gamma |
| Alzheimer's disease | theta | gamma |
| Alzheimer's disease | delta | gamma |
| depression | alpha | gamma |
| depression | theta | gamma |
| bipolar disorder | delta | alpha |
| bipolar disorder | theta | gamma |

Methods of the present invention may be used to enhance any suitable cognitive trait, including, but not limited to, alertness, awareness, memory accuracy, memory longevity, information processing accuracy and information processing speed. In some embodiments, methods of the present invention are used to enhance problem-solving ability. In some embodiments, one or more OECs in the gamma frequency band is passed through the skull of the subject to enhance a subject's alertness, awareness, memory accuracy, memory longevity, information processing accuracy and information processing speed. In some embodiments, one or more OECs in the gamma frequency band is passed through the skull of the subject to enhance a subject's problem-solving ability.

Methods of the present invention may be used to enhance one or more cognitive traits by at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 250%, 300% or more.

Methods of the present invention may be used to enhance creativity. In some embodiments, one or more OECs in the alpha frequency band is passed through the skull of the subject to enhance a subject's creativity. Creativity may be measured by techniques known in the art, such as the Torrance Test of Creativity Thinking.

Methods of the present invention may be used to enhance creativity by at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 250%, 300% or more.

Methods of the present invention may be used to modulate the cortical state of a subject in any suitable manner, including, but not limited to, increasing the likelihood of transitioning from an inactive state to an active state, decreasing the likelihood of transitioning from an inactive state to an active state, increasing the likelihood of transitioning from an active state to an inactive state, decreasing the likelihood of transitioning from an active state to an inactive state, increasing the likelihood of transitioning between active states, decreasing the likelihood of transitioning between active states, increasing the likelihood of transitioning between inactive states, decreasing the likelihood of transitioning between inactive states, increasing the likelihood of remaining in an active state, decreasing the likelihood of remaining in an active state, increasing the likelihood of remaining in an inactive state, decreasing the likelihood of remaining in an inactive state, increasing the duration of an active state, decreasing the duration of an active state, increasing the duration of an inactive state and decreasing the duration of an inactive state. In some embodiments, one or more OECs in the gamma frequency band is passed through the skull of the subject to increase the likelihood of transitioning from an inactive state to an active state, decrease the likelihood of transitioning from an active state to an inactive state, increase the likelihood of transitioning between active states, increase the likelihood of remaining in an active state, decrease the likelihood of remaining in an inactive state, increase the duration of an active state and/or decrease the duration of an inactive state. In some embodiments, one or more OECs in the alpha frequency band is passed through the skull of the subject to increase the likelihood of transitioning from an active state to an inactive state, decrease the likelihood of transitioning from an inactive state to an active state, increase the likelihood of transitioning between inactive states, increase the likelihood of remaining in an inactive state, decrease the likelihood of remaining in an active state, increase the duration of an inactive state and/or decrease the duration of an active state.

Cortical Stimulation Devices

The present invention provides cortical stimulation devices (CSDs) capable of detecting cortical oscillations and/or coherence (e.g., coherence between cortical oscillations of a specific frequency (or group of frequencies)) in a subject and/or passing one or more OECs through the skull of a subject. In some embodiments, the device provides transcranial alternating current stimulation (tACS) and/or transcranial direct current stimulation (tDCS).

CSDs of the present invention may be configured to perform any method described herein.

CSDs of the present invention may comprise any suitable module/component. In some embodiments, the CSD comprises, consists essentially of or consists of a module/component configured to detect cortical oscillations in a subject, a module/component configured to analyze cortical oscillations, a module/component configured to generate one or more OECs, a module/component configured to pass one or more OECs through the skull of the subject, a module/component configured to collect, generate, store and/or transmit data associated with the administration of one or more OECs and/or a module/component configured to retrieve, receive and/or store instructions for administering one or more OECs.

CSDs of the present invention may comprise any suitable means of detecting cortical oscillations, including, but not limited to, electroencephalograms, electrocardiograms, pupilometers and/or a functional near-infrared spectrometers. In some embodiments, the detection module/component comprises, consists essentially of or consists of an electroencephalogram (e.g., a modular electroencephalogram system such as the one described in Example 1). In some embodiments, the detection module/component comprises, consists essentially of or consists of a module/component configured to detect cortical oscillations by identifying one or more changes in the subject's pupil diameter, the subject's skin conductance, the subject's heart rate and/or the regularity of the subject's heartbeat.

CSDs of the present invention may be configured to detect any suitable cortical oscillations, including, but not limited to, cortical oscillations that oscillate in the alpha frequency band, cortical oscillations that oscillate in the beta frequency band, cortical oscillations that oscillate in the delta frequency band, cortical oscillations that oscillate in the gamma frequency band and/or cortical oscillations that oscillate in the theta frequency band.

CSDs of the present invention may be configured to detect cortical oscillations in any suitable region(s) of a subject's brain, including, but not limited to, the subject's occipital lobe, parietal lobe, temporal lobe, frontal lobe, visual cortex, auditory cortex, somatosensory cortex, premotor cortex, subject's motor cortex, prefrontal cortex, Wernicke's area, Broca's area, sensory association area, auditory association area and/or visual association area. In some embodiments, the CSD is configured to detect cortical oscillations in two or more regions of the subject's brain concurrently. In some embodiments, the CSD is configured to detect cortical oscillations in two or more regions of the subject's brain sequentially. For example, CSDs of the present invention may be configured to concurrently/sequentially detect cortical oscillations in the auditory cortex, the prefrontal cortex and/or temporoparietal cortex of the subject's brain (in a subject with schizophrenia, for example). In some embodiments, the CSD is configured to concurrently/sequentially detect cortical oscillations in the subject's premotor cortex and/or primary motor cortex (in a subject with a movement disorder, for example).

CSDs of the present invention may comprise any suitable means of analyzing cortical oscillations, including, but not limited to, modules/components configured to calculate the difference between the magnitude of the cortical oscillations and a target value, the difference between the magnitude of the cortical oscillations and an upper threshold, the difference between the magnitude of the cortical oscillations and a lower threshold, the variance of the magnitude of the cortical oscillations over a defined period of time, the difference between the variance of the magnitude of the cortical oscillations and a target value, the difference between the variance of the magnitude of the cortical oscillations over a defined period of time and an upper threshold, the difference between the variance of the magnitude of the cortical oscillations over a defined period of time and a lower threshold, the integral of the magnitude of the cortical oscillations, the difference between the integral of the magnitude of the cortical oscillations and a target value, the difference between the integral of the magnitude of the cortical oscillations and an upper threshold, the difference between the integral of the magnitude of the cortical oscillations and a lower threshold, the temporal derivative of the magnitude of the cortical oscillations, the difference between the temporal derivative of the magnitude of the cortical oscillations and a target value, the difference between the temporal derivative of the magnitude of the cortical oscillations and an upper threshold, the difference between the temporal derivative of the magnitude of the cortical oscillations and a lower threshold, the average magnitude of the cortical oscillations over a defined period of time, the difference between the average magnitude of the cortical oscillations over a defined period of time and a target value, the difference between the average magnitude of the cortical oscillations over a defined period of time and an upper threshold, the difference between the average magnitude of the cortical oscillations over a defined period of time and a lower threshold, the variance of the average magnitude of the cortical oscillations over a defined period of time, the difference between the variance of the average magnitude of the cortical oscillations over a defined period of time and a target value, the difference between the variance of the average magnitude of the cortical oscillations over a defined period of time and an upper threshold, the difference between the variance of the average magnitude of the cortical oscillations over a defined period of time and a lower threshold, the integral of the average magnitude of the cortical oscillations over a defined period of time, the difference between the integral of the average magnitude of the cortical oscillations over a defined period of time and a target value, the difference between the integral of the average magnitude of the cortical oscillations over a defined period of time and an upper threshold, the difference between the integral of the average magnitude of the cortical oscillations over a defined period of time and a lower threshold, the temporal derivative of the average magnitude of the cortical oscillations over a defined period of time, the difference between the temporal derivative of the average magnitude of the cortical oscillations over a defined period of time and a target value, the difference between the temporal derivative of the average magnitude of the cortical oscillations over a defined period of time and an upper threshold, the difference between the temporal derivative of the average magnitude of the cortical oscillations over a defined period of time and a lower threshold, to what degree the cortical oscillations in a first brain region are synchronized, the difference between the degree of synchronization of the cortical oscillations within a first brain region and a target value, the difference between the degree of synchronization of the cortical oscillations within a first brain region and an upper threshold, the difference between the degree of synchronization of the cortical oscillations within a first brain region and a lower threshold, the variance of the degree of synchronization of the cortical oscillations within a first brain region over a defined period of time, the difference between the variance of the degree of synchronization of the cortical oscillations within a first brain region and a target value, the difference between the variance of the degree of synchronization of the cortical oscillations within a first brain region and an upper threshold, the difference between the variance of the degree of synchronization of the cortical oscillations within a first brain region and a lower threshold, the average degree of synchronization of the cortical oscillations within a first brain region over a defined period of time, the difference between the average degree of synchronization of the cortical oscillations within a first brain region and a target value, the difference between the average degree of synchronization of the cortical oscillations within a first brain region and an upper threshold, the difference between the average degree of synchronization of the cortical oscillations within a first brain region and a lower threshold, the variance of the average degree of synchronization of the cortical oscillations within a first brain region over a defined period of time, the difference between the variance of the average degree of synchronization of the cortical oscillations within a first brain region and a target value, the difference between the variance of the average degree of synchronization of the cortical oscillations within a first brain region and an upper threshold, the difference between the variance of the average degree of synchronization of the cortical oscillations within a first brain region and a lower threshold, to what degree the cortical oscillations in a first brain region are synchronized with the cortical oscillations in a second brain region, the difference between the degree of synchronization between the cortical oscillations in a first brain region and the cortical oscillations in a second brain region and a target value, the difference between the degree of synchronization between the cortical oscillations in a first brain region and the cortical oscillations in a second brain region and an upper threshold, the difference between the degree of synchronization of the cortical oscillations between the cortical oscillations in a first brain region and the cortical oscillations in a second brain region and a lower threshold, the variance of the degree of synchronization of the cortical oscillations between the cortical oscillations in a first brain region and the cortical oscillations in a second brain region over a defined period of time, the difference between the variance of the degree of synchronization of the cortical oscillations between the cortical oscillations in a first brain region and the cortical oscillations in a second brain region and a target value, the difference between the variance of the degree of synchronization of the cortical oscillations between the cortical oscillations in a first brain region and the cortical oscillations in a second brain region and an upper threshold, the difference between the variance of the degree of synchronization of the cortical oscillations between the cortical oscillations in a first brain region and the cortical oscillations in a second brain region and a lower threshold, the average degree of synchronization of the cortical oscillations between the cortical oscillations in a first brain region and the cortical oscillations in a second brain region over a defined period of time, the difference between the average degree of synchronization of the cortical oscillations between the cortical oscillations in a first brain region and the cortical oscillations in a second brain region and a target value, the difference between the average degree of synchronization of the cortical oscillations between the cortical oscillations in a first brain region and the cortical oscillations in a second brain region and an upper threshold, the difference between the average degree of synchronization of the cortical oscillations between the cortical oscillations in a first brain region and the cortical oscillations in a second brain region and a lower threshold, the variance of the average degree of synchronization of the cortical oscillations between the cortical oscillations in a first brain region and the cortical oscillations in a second brain region over a defined period of time, the difference between the variance of the average degree of synchronization of the cortical oscillations between the cortical oscillations in a first brain region and the cortical oscillations in a second brain region and a target value, the difference between the variance of the average degree of synchronization of the cortical oscillations between the cortical oscillations in a first brain region and the cortical oscillations in a second brain region and an upper threshold, and/or the difference between the variance of the average degree of synchronization of the cortical oscillations between the cortical oscillations in a first brain region and the cortical oscillations in a second brain region and a lower threshold. In some embodiments, the analysis module/component comprises, consists essentially of or consists of a module/component configured to analyze cortical oscillations in real time (e.g., a RealTime eXperiment Interface such as the one described in Example 1).

CSDs of the present invention may comprise any suitable means of generating one or more OECs, including, but not limited to, modules/components configured to generate one or more OECs, the magnitude of which is/are proportional to one or more characteristics of cortical oscillations detected in one or more regions of a subject's brain. In some embodiments, the CSD comprises, consists essentially of or consists of a module/component configured to generate one or more OECs in real-time responsive to analysis of cortical oscillations in a subject's brain, to generate an OEC with a magnitude sufficient to prevent cortical oscillations in a subject's brain from exceeding an upper threshold, to generate an OEC with a magnitude sufficient to prevent cortical oscillations in a subject's brain from falling below a lower threshold, to generate an OEC with a magnitude sufficient to increase the synchronization of cortical oscillations within a first brain region of a subject's brain, to generate an OEC with a magnitude sufficient to increase the synchronization of cortical oscillations in a first region of a subject's brain with cortical oscillations in a second region of the subject's brain, to generate an OEC with a magnitude sufficient to decrease the synchronization of cortical oscillations within a first region of a subject's brain, to generate an OEC with a magnitude sufficient to decrease the synchronization of cortical oscillations in a first region of a subject's brain with cortical oscillations in a second region of the subject's brain, to generate an OEC that oscillates in the alpha frequency band, to generate an OEC that oscillates in the beta frequency band, to generate an OEC that oscillates in the delta frequency band, to generate an OEC that oscillates in the gamma frequency band and/or to generate an OEC that oscillates in the theta frequency band. In some embodiments, the generation module/component comprises, consists essentially of or consists of a proportional-integral-derivative controller. In some embodiments, the generation module/component comprises, consists essentially of or consists of a module/component configured to generate one or more OECs in real time (e.g., a RealTime eXperiment Interface such as the one described in Example 1).

CSDs of the present invention may comprise any suitable means for passing the OEC(s) through the skull of the subject, including, but limited to, modules/components comprising one or more pairs of electrodes. In some embodiments, the OEC passing module/component comprises, consists essentially of or consists of one or more pairs of electrodes configured to pass one or more OECs through the skull of the subject (e.g., a pair of electrodes sheathed in saline-soaked sponges as described in Example 1). Such electrodes may be configured for placement at any suitable position(s) on the scalp, including, but not limited to, the positions defined by the International 10-20 System of Electrode Placement.

CSDs of the present invention may be configured to pass OECs into any suitable region(s) of a subject's brain, including, but not limited to, the subject's occipital lobe, parietal lobe, temporal lobe, frontal lobe, visual cortex, auditory cortex, somatosensory cortex, premotor cortex, subject's motor cortex, prefrontal cortex, Wernicke's area, Broca's area, sensory association area, auditory association area and/or visual association area. In some embodiments, the CSD is configured to pass OECs into two or more regions of the subject's brain concurrently. In some embodiments, the CSD is configured to pass OECs into two or more regions of the subject's brain sequentially. For example, the CSD may be configured to concurrently/sequentially pass OECs into the auditory cortex, the prefrontal cortex and/or temporoparietal cortex of the subject's brain (in a subject with schizophrenia, for example). In some embodiments, the CSD is configured to concurrently/sequentially pass OECs into the subject's premotor cortex and/or primary motor cortex (in a subject with a movement disorder, for example).

CSDs of the present invention may comprise any suitable means for collecting, generating, storing and/or transmitting data associated with the administration of one or more OECs. In some embodiments, the CSD comprises a module/component configured to collect data associated with the administration of one or more OECs from an analysis module, a generation module and/or a OEC passing module, to store data associated with the administration of one or more OECs in a database and/or to transmit data associated with the administration of one or more OECs.

CSDs of the present invention may comprise any suitable means for retrieving, receiving and/or storing instructions for administering one or more OECs. In some embodiments, the CSD comprises a module/component configured to receive/retrieve instructions for administering one or more OECs from a cortical stimulation planning device and/or to store instructions for administering one or more OECs in a database.

CSDs of the present invention may be configured to transmit/receive/retrieve data over any suitable wired or wireless communications channel, including, but not limited to, a LAN, the Internet, a public telephone switching network, Bluetooth, WLAN and the like.

CSDs of the present invention may comprise one or more modules/components configured to detect cortical oscillations and generate/deliver OECs. In some embodiments, the CSD comprises, consists essentially of or consists of a module/component that is configured to detect cortical oscillations that oscillate in a first frequency band and generate an OEC that oscillates in the first frequency band, to detect cortical oscillations that oscillate in a first frequency band and generate an OEC that oscillates in a second frequency band different from the first frequency band, to detect cortical oscillations in a first brain region and pass the OEC through the skull of the subject into the first brain region and/or to detect cortical oscillations in a first brain regions and pass the OEC through the skull of the subject into a second brain region different from the first brain region.

The present invention provides CSDs capable of passing one or more OECs through the skull of a subject. The CSD can be used, for example in clinical trials, in a physician's office or at a subject's home. In some embodiments, the CSD provides two-channel transcranial current stimulation (both tACS and tDCS). In certain embodiments, both channels can be independently programmed yet do not exhibit phase drift, and can be guaranteed to remain synchronized if matched frequencies are chosen (applicable for tACS). Arbitrary sham waveforms (any combination of tACS and tDCS) can be programmed, e.g., for use in clinical trials. In certain embodiments, the CSD is powered by a battery (e.g., a single 9V battery) so that no charger or power supply is required.

In some embodiments, the CSD is controlled by an application, e.g., one that can run on a tablet or smartphone. This enhances stimulation success as operation of the device is incredibly simple. The tablet or smartphone may connect to the CSD wirelessly (e.g., using Bluetooth) or using a cable. In certain embodiments, the application that controls the CSD may also collect data about the quality of the stimulation (electrode impedance) and may optionally submit such data (e.g., detailed stimulator logs) to a centralized database or other location. One advantage of using an application to program the device is that additional functionality can be easily added as it requires only an upgrade of the application, not the device.

In some embodiments, the CSD can be set to a "remote control mode" such that the stimulation parameters are downloaded to the application from an outside source (e.g., a secure internet portal). This allows a physician to control the CSD, allowing both high quality clinical trials and home use of the device by physician prescription. In certain embodiments, the CSD can be locked (e.g., by the application) such that the end-user can only start the stimulation, for example by pressing a single (and only) button on the CSD. In certain embodiments, the button may change color and/or functionality during stimulation (e.g., switches from green to red and/or serves as an emergency stop).

In some embodiments, the CSD includes safety features that may include one or more of continuous stimulation current, voltage, and impedance monitoring and hardware-based automatic power shutdown of both stimulation and overall device power supply.

In one embodiment, the CSD may comprise or consist of one or more of the following main components/subsystems: (1) tablet with user interface application (App); (2) microprocessor; (3) function generator chip; (4) voltage controlled current source; and (5) safety circuitry. In this embodiment, the stimulation parameters are specified by the user through the application. The parameters may include, but are not limited to, one or more of the following: (1) tDCS/tACS; (2) number of channels; (3) amplitude; (4) test duration; (5) frequency (for tACS); and (6) password. Next, the parameters are sent via Bluetooth to the microprocessor. The microprocessor interprets these parameters, and programs the function generator chip accordingly through a serial peripheral interface. The function generator then creates the programmed waveform, which is ultimately a voltage signal. The voltage signal is applied to a voltage controlled current source, which generates the specified amount of current through an arbitrary load resistance.

Cortical Stimulation Planning Devices

The present invention provides cortical stimulation planning devices (CSPDs) capable of analyzing data associated with the administration of one or more OECs and/or generating/transmitting instructions for administering one or more OECs.

CSPDs of the present invention may comprise any suitable module/component. In some embodiments, the CSPD comprises, consists essentially of or consists of a module/component configured to receive, retrieve and/or store data associated with the administration of one or more OECs, a module/component configured to analyze data associated with the administration of one or more OECs and/or a module/component configured to generate, store and/or transmit instructions for administering one or more OECs.

CSPDs of the present invention may comprise any suitable means of analyzing data associated with the administration of one or more OECs, including, but not limited to, analyzing the efficiency of a given treatment session/regimen and/or comparing the results of a first treatment session/regimen with one or more other treatment sessions/regimens. In some embodiments, the CSPD comprises a module/component configured to compare the results of a treatment session/regimen administered to a first subject with one or more treatment sessions/regimens administered to another subject (or to a group of other subjects).

CSPDs of the present invention may be configured to generate instructions for administering any suitable cortical oscillations, including, but not limited to, cortical oscillations that oscillate in the alpha frequency band, cortical oscillations that oscillate in the beta frequency band, cortical oscillations that oscillate in the delta frequency band, cortical oscillations that oscillate in the gamma frequency band and/or cortical oscillations that oscillate in the theta frequency band.

CSPDs of the present invention may be configured to generate any suitable instructions for administering one or more OECs, including, but not limited to, increasing/decreasing one or more target values (e.g., the target value for the degree of synchronization between two brain regions with respect to cortical oscillations in the gamma frequency band), increasing/decreasing one or more upper thresholds (e.g., an upper threshold for the magnitude cortical oscillations in the alpha frequency band), increasing/decreasing one or more lower thresholds (e.g., a lower threshold for the magnitude cortical oscillations in the gamma frequency band).

CSPDs of the present invention may comprise any suitable means for receiving, retrieving and/or storing data associated with the administration of one or more OECs. In some embodiments, the CSPD comprises a module/component configured to receive/retrieve data associated with the administration of one or more OECs from a CSD (e.g., a CSD of the present invention) and/or to store data associated with the administration of one or more OECs in a database.

CSPDs of the present invention may comprise any suitable means for generating, storing and/or transmitting instructions for administering one or more OECs. In some embodiments, the CSPD comprises a module/component configured to generate instructions for administering one or more OECs, to store instructions for administering one or more OECs in a database and/or to transmit instructions for administering one or more OECs to a CSD (e.g., a CSD of the present invention).

CSPDs of the present invention may be configured to transmit/receive/retrieve data over any suitable wired or wireless communications channel, including, but not limited to, a LAN, the Internet, a public telephone switching network, Bluetooth, WLAN and the like.

Computer Program Products

The present invention provides computer program products for detecting cortical oscillations and/or coherence (e.g., coherence between cortical oscillations of a specific frequency (or group of frequencies)) in a subject and/or passing one or more OECs through the skull of a subject.

Computer program products of the present invention may be useful for modulating cortical activity, modulating cortical states, enhancing one or more cognitive traits and/or treating one or more neurological disorders.

Computer program products of the present invention may comprise any suitable computer-readable program code. In some embodiments, the computer program product comprises, consists essentially of or consists of a computer-readable storage medium having computer-readable program code embodied therein, the computer-readable program code comprising computer-readable program code to perform any method described herein. In some embodiments, the computer program product comprises, consists essentially of or consists of a computer-readable storage medium having computer-readable program code embodied therein, the computer-readable program code comprising computer-readable program code to detect cortical oscillations in a subject, to analyze cortical oscillations, to generate one or more OECs and/or to pass one or more OECs through the skull of the subject. In some embodiments, the computer program product comprises, consists essentially of or consists of a computer-readable storage medium having computer-readable program code embodied therein, the computer-readable program code comprising computer-readable program code to detect cortical oscillations that oscillate in the alpha frequency band, to detect cortical oscillations that oscillate in the beta frequency band, to detect cortical oscillations that oscillate in the delta frequency band, to detect cortical oscillations that oscillate in the gamma frequency band, and/or to detect cortical oscillations that oscillate in the theta frequency band. In some embodiments, the computer program product comprises, consists essentially of or consists of a computer-readable storage medium having computer-readable program code embodied therein, the computer-readable program code comprising computer-readable program code to calculate the difference between the magnitude of the cortical oscillations and a target value, the difference between the magnitude of the cortical oscillations and an upper threshold, the difference between the magnitude of the cortical oscillations and a lower threshold, the variance of the magnitude of the cortical oscillations over a defined period of time, the difference between the variance of the magnitude of the cortical oscillations and a target value, the difference between the variance of the magnitude of the cortical oscillations over a defined period of time and an upper threshold, the difference between the variance of the magnitude of the cortical oscillations over a defined period of time and a lower threshold, the integral of the magnitude of the cortical oscillations, the difference between the integral of the magnitude of the cortical oscillations and a target value, the difference between the integral of the magnitude of the cortical oscillations and an upper threshold, the difference between the integral of the magnitude of the cortical oscillations and a lower threshold, the temporal derivative of the magnitude of the cortical oscillations, the difference between the temporal derivative of the magnitude of the cortical oscillations and a target value, the difference between the temporal derivative of the magnitude of the cortical oscillations and an upper threshold, the difference between the temporal derivative of the magnitude of the cortical oscillations and a lower threshold, the average magnitude of the cortical oscillations over a defined period of time, the difference between the average magnitude of the cortical oscillations over a defined period of time and a target value, the difference between the average magnitude of the cortical oscillations over a defined period of time and an upper threshold, the difference between the average magnitude of the cortical oscillations over a defined period of time and a lower threshold, the variance of the average magnitude of the cortical oscillations over a defined period of time, the difference between the variance of the average magnitude of the cortical oscillations over a defined period of time and a target value, the difference between the variance of the average magnitude of the cortical oscillations over a defined period of time and an upper threshold, the difference between the variance of the average magnitude of the cortical oscillations over a defined period of time and a lower threshold, the integral of the average magnitude of the cortical oscillations over a defined period of time, the difference between the integral of the average magnitude of the cortical oscillations over a defined period of time and a target value, the difference between the integral of the average magnitude of the cortical oscillations over a defined period of time and an upper threshold, the difference between the integral of the average magnitude of the cortical oscillations over a defined period of time and a lower threshold, the temporal derivative of the average magnitude of the cortical oscillations over a defined period of time, the difference between the temporal derivative of the average magnitude of the cortical oscillations over a defined period of time and a target value, the difference between the temporal derivative of the average magnitude of the cortical oscillations over a defined period of time and an upper threshold, the difference between the temporal derivative of the average magnitude of the cortical oscillations over a defined period of time and a lower threshold, to what degree the cortical oscillations in a first brain region are synchronized, the difference between the degree of synchronization of the cortical oscillations within a first brain region and a target value, the difference between the degree of synchronization of the cortical oscillations within a first brain region and an upper threshold, the difference between the degree of synchronization of the cortical oscillations within a first brain region and a lower threshold, the variance of the degree of synchronization of the cortical oscillations within a first brain region over a defined period of time, the difference between the variance of the degree of synchronization of the cortical oscillations within a first brain region and a target value, the difference between the variance of the degree of synchronization of the cortical oscillations within a first brain region and an upper threshold, the difference between the variance of the degree of synchronization of the cortical oscillations within a first brain region and a lower threshold, the average degree of synchronization of the cortical oscillations within a first brain region over a defined period of time, the difference between the average degree of synchronization of the cortical oscillations within a first brain region and a target value, the difference between the average degree of synchronization of the cortical oscillations within a first brain region and an upper threshold, the difference between the average degree of synchronization of the cortical oscillations within a first brain region and a lower threshold, the variance of the average degree of synchronization of the cortical oscillations within a first brain region over a defined period of time, the difference between the variance of the average degree of synchronization of the cortical oscillations within a first brain region and a target value, the difference between the variance of the average degree of synchronization of the cortical oscillations within a first brain region and an upper threshold, the difference between the variance of the average degree of synchronization of the cortical oscillations within a first brain region and a lower threshold, to what degree the cortical oscillations in a first brain region are synchronized with the cortical oscillations in a second brain region, the difference between the degree of synchronization between the cortical oscillations in a first brain region and the cortical oscillations in a second brain region and a target value, the difference between the degree of synchronization between the cortical oscillations in a first brain region and the cortical oscillations in a second brain region and an upper threshold, the difference between the degree of synchronization of the cortical oscillations between the cortical oscillations in a first brain region and the cortical oscillations in a second brain region and a lower threshold, the variance of the degree of synchronization of the cortical oscillations between the cortical oscillations in a first brain region and the cortical oscillations in a second brain region over a defined period of time, the difference between the variance of the degree of synchronization of the cortical oscillations between the cortical oscillations in a first brain region and the cortical oscillations in a second brain region and a target value, the difference between the variance of the degree of synchronization of the cortical oscillations between the cortical oscillations in a first brain region and the cortical oscillations in a second brain region and an upper threshold, the difference between the variance of the degree of synchronization of the cortical oscillations between the cortical oscillations in a first brain region and the cortical oscillations in a second brain region and a lower threshold, the average degree of synchronization of the cortical oscillations between the cortical oscillations in a first brain region and the cortical oscillations in a second brain region over a defined period of time, the difference between the average degree of synchronization of the cortical oscillations between the cortical oscillations in a first brain region and the cortical oscillations in a second brain region and a target value, the difference between the average degree of synchronization of the cortical oscillations between the cortical oscillations in a first brain region and the cortical oscillations in a second brain region and an upper threshold, the difference between the average degree of synchronization of the cortical oscillations between the cortical oscillations in a first brain region and the cortical oscillations in a second brain region and a lower threshold, the variance of the average degree of synchronization of the cortical oscillations between the cortical oscillations in a first brain region and the cortical oscillations in a second brain region over a defined period of time, the difference between the variance of the average degree of synchronization of the cortical oscillations between the cortical oscillations in a first brain region and the cortical oscillations in a second brain region and a target value, the difference between the variance of the average degree of synchronization of the cortical oscillations between the cortical oscillations in a first brain region and the cortical oscillations in a second brain region and an upper threshold, and/or the difference between the variance of the average degree of synchronization of the cortical oscillations between the cortical oscillations in a first brain region and the cortical oscillations in a second brain region and a lower threshold. In some embodiments, the computer program product comprises, consists essentially of or consists of a computer-readable storage medium having computer-readable program code embodied therein, the computer-readable program code comprising computer-readable program code to generate an OEC in real-time responsive to analysis of cortical oscillations, to generate an OEC with a magnitude sufficient to prevent the cortical oscillations from exceeding an upper threshold, to generate an OEC with a magnitude sufficient to prevent the cortical oscillations from falling below a lower threshold, to generate an OEC with a magnitude sufficient to increase the synchronization of the cortical oscillations within a first brain region, to generate an OEC with a magnitude sufficient to increase the synchronization of the cortical oscillations in a first brain region with the cortical oscillations in a second brain region, to generate an OEC with a magnitude sufficient to decrease the synchronization of the cortical oscillations within a first brain region, to generate an OEC with a magnitude sufficient to decrease the synchronization of the cortical oscillations in a first brain region with the cortical oscillations in a second brain region, to generate an OEC that oscillates in the alpha frequency band, to generate an OEC that oscillates in the beta frequency band, to generate an OEC that oscillates in the delta frequency band, to generate an OEC that oscillates in the gamma frequency band, and/or to generate an OEC that oscillates in the theta frequency band. In some embodiments, the computer program product comprises, consists essentially of or consists of a computer-readable storage medium having computer-readable program code embodied therein, the computer-readable program code comprising computer-readable program code to detect cortical oscillations and generate/deliver OECs. In some embodiments, the computer program product comprises, consists essentially of or consists of a computer-readable storage medium having computer-readable program code embodied therein, the computer-readable program code comprising computer-readable program code to detect cortical oscillations that oscillate in a first frequency band and to generate an OEC that oscillates in the first frequency band, to detect cortical oscillations that oscillate in a first frequency band and to generate an OEC that oscillates in a second frequency band different from the first frequency band, to detect cortical oscillations in a first brain region and to pass the OEC through the skull of the subject into the first brain region and/or to detect cortical oscillations in a first brain regions and to pass the OEC through the skull of the subject into a second brain region different from the first brain region.

Computer Systems

The present invention provides computer systems for modulating cortical activity, modulating cortical states, enhancing one or more cognitive traits and/or treating one or more neurological disorders.

Computer systems of the present invention may comprise any suitable device, including, but not limited to, CSDs and cortical stimulation planning devices (CSPDs). In some embodiments, the computer system comprises, consists essentially of or consists of a CSPD of the present invention and one or more CSDs of the present invention.

Computer systems of the present invention may comprise, consist essentially of or consist of a CSD configured to detect cortical oscillations in a subject, to analyze the detected cortical oscillations, to administer one or more OECs through the skull of the subject responsive to analysis of the detected cortical oscillations and to transmit data associated with the administration of the OEC(s) to a CSPD that is configured to analyze the data associated with the administration of the OEC(s) and to transmit instructions to the CSD responsive to analysis of the data associated with the administration of the OEC(s). The CSD and CSPD may be configured to relay data over any suitable wired or wireless communications channel, including, but not limited to, a LAN, the Internet, a public telephone switching network, Bluetooth, WLAN and the like.

Having described the present invention, the same will be explained in greater detail in the following examples, which are included herein for illustration purposes only, and which are not intended to be limiting to the invention.

EXAMPLE 1

Brain stimulation has gained momentum as an alternative to pharmacological approaches for the treatment of neurological disorders. Although direct targeting of aberrant network dynamics in the brain with electric stimulation offers the opportunity to deliver individualized stimulation with potentially higher efficacy and less undesired side-effects, most of the currently studied stimulation approaches are feedforward systems where the stimulation waveform is preprogrammed. Given the vast success of feedback control in a broad range of engineering applications, we hypothesized that applying stimulation that adapts to simultaneously recorded brain activity may provide better control of dynamics in cerebral cortex, the brain structure responsible for cognition and implicated in many psychiatric illnesses.

We combined transcranial alternating current stimulation (tACS) with EEG to control state dynamics in visual cortex of humans. tACS applies a weak, sine-wave electric current to the scalp. The resulting electric field modulates neuronal network activity by changing the polarization of a large number of neurons. Huang et al., Y. Z., BRAIN STIMUL. 2(1):2 (2009); Kanai, et al., CLIN. NEUROPHYSIOL. 121(9):1551 (2010); Zaghi et al., NEUROSCIENTIST, 16(3):285 (2010); Schutter et al., BRAIN STIMUL. 4(2):97 (2011); Polania et al., CURR. BIOL. 22(14):1314 (2012). Early evidence suggests that sine-wave stimulation waveforms can be used to selectively modulate cortical oscillations at different frequencies that are commonly associated with different cognitive states. Wang et al., PHYSIOL. REV. 90(3):1195 (2010). We have recently found (unpublished data) that cortical oscillations in the alpha band (8-12 Hz) are antagonistically modulated by tACS at 40 Hz in the gamma band. In essence, tACS at 40 Hz enhances the intrinsic antagonism between resting-state, alpha rhythms and sensory-processing, gamma rhythms. We here show results from our pilot study with our feedback tACS system where we managed to successfully suppress the state-dynamics between high- and low-alpha states induced by opening and closing the eyes. To our knowledge, this is the first successful demonstration of feedback tACS to control cortical state dynamics. Given the known aberrations in state dynamics in subjects with psychiatric illnesses such as schizophrenia, autism, and depression (Uhlhaas et al., NEURON 75(6):963 (2012)), our system provides a starting point for the development of the next generation non-invasive brain stimulation that provides targeted and individualized stimulation by feedback control.

I. Methods

A. System Design

A closed-loop EEG feedback-controlled tACS (FB tACS) system comprising commercially available and custom-made hardware and software (FIG. 1A) was used to simultaneously process EEG data and apply tACS such that endogenous brain activity dynamically informed stimulation decisions.

EEG data were obtained using a modular data acquisition system (BIOPAC Systems, Inc., Goleta, Calif.) comprising an isolated power supply (ISP100C), a single-channel EEG amplifier with adjustable gain (G=50,000), an amplifier (EEG100C-MRI), a high level transducer module (HLT100C) and an output signal isolation adapter (OUT-ISO).

The raw EEG data were transmitted to a custom-designed interface box. This box enabled safe communication between the computer and analog input/output devices (input: raw EEG signal, output: stimulation waveform). Both input and output signals were passed through circuit elements that limited current, voltage, and frequency. The input signal was fed into a NI PCI-6221 data acquisition device (DAQ) (National Instruments Corporation, Austin, Tex.), that in turn provided the output signal. The safety elements combined a thermistor with trip current of 17 mA, a transient-voltage-suppression (TVS) diode with a trip voltage of 11.1V, and a passive resistor-capacitor (RC) low-pass filter with a cutoff frequency of 100 Hz. The purpose of the safety-circuit was to protect both the human subject and the equipment in the unlikely case of an undesired voltage or current transient.

We used the RealTime eXperiment Interface (RTXI; www.rtxi.org) with COMEDI drivers (comedi.org; used to communicate with the DAQ) to process the incoming EEG signal and compute the output stimulation waveform in real-time.

We implemented our stimulation paradigms as RTXI C++ modules that specified the input and output channels and the required signal processing. Specifically, the FB tACS system read in the signal from the EEG amplifier as an analog input, processed and stored the data using RTXI, and output the stimulation waveform to an analog output port on the DAQ in real-time. This stimulation output was fed into the "remote input" BNC connector of a NeuroConn DC-STIMULATOR PLUS (neuroConn GmbH, Ilmenau, Germany).

We used the DC-STIMULATOR PLUS as a voltage-controlled current source (VCCS) with a transfer gain of 2 mA/V. Therefore, a 40 Hz, 1V peak-to-peak sinusoidal oscillation on the remote input produced a 40 Hz, 2 mA peak-to-peak sinusoidal oscillation through the stimulating electrodes. When in remote mode, the DC-STIMULATOR PLUS constantly output a current, and even if the remote input was held at 0V, we found that a small DC current was applied through the stimulating electrodes. To prevent this offset, we designed the FB tACS system to continuously output a 40 Hz waveform, but modulated the amplitude to effectively turn on and off stimulation. When the stimulation amplitude was 0.1 mA peak-to-peak, the stimulation was considered "off", and when the stimulation amplitude was 1.0 mA peak-to-peak, the stimulation was considered "on". We used two standard 5×7 cm rubber electrodes sheathed in saline-soaked sponges.

B. Controller Design

The controller first filtered the raw EEG data (fs=2 kHz) with a 6th order infinite impulse response (IIR) Butterworth band-pass filter (cutoff frequencies at 8 and 12 Hz) to isolate power in the alpha band. Power in the alpha band was calculated as the mean oscillation power (V2) during 1 s windows. The controller built a distribution of those binned alpha-power values for the duration of the calibration period and determined the median alpha power. Two separate values were computed for eyes open and eyes closed (first and second 60 s of calibration period, respectively). Stimulation threshold was set to 1.05 of the average of these two values. The subsequent online analysis calculated mean alpha power during the last 1 s of each consecutive 4 s window and compared it to the stimulation threshold. If alpha power was higher than the stimulation threshold, the FB tACS system applied 1.0 mA peak-to-peak 40 Hz tACS for the first 2 s of the next window. Otherwise, the controller continuously applied 0.1 mA peak-to-peak 40 Hz tACS for the entire recording (FIG. 1B).

C. Experimental Procedures

Figure 2:
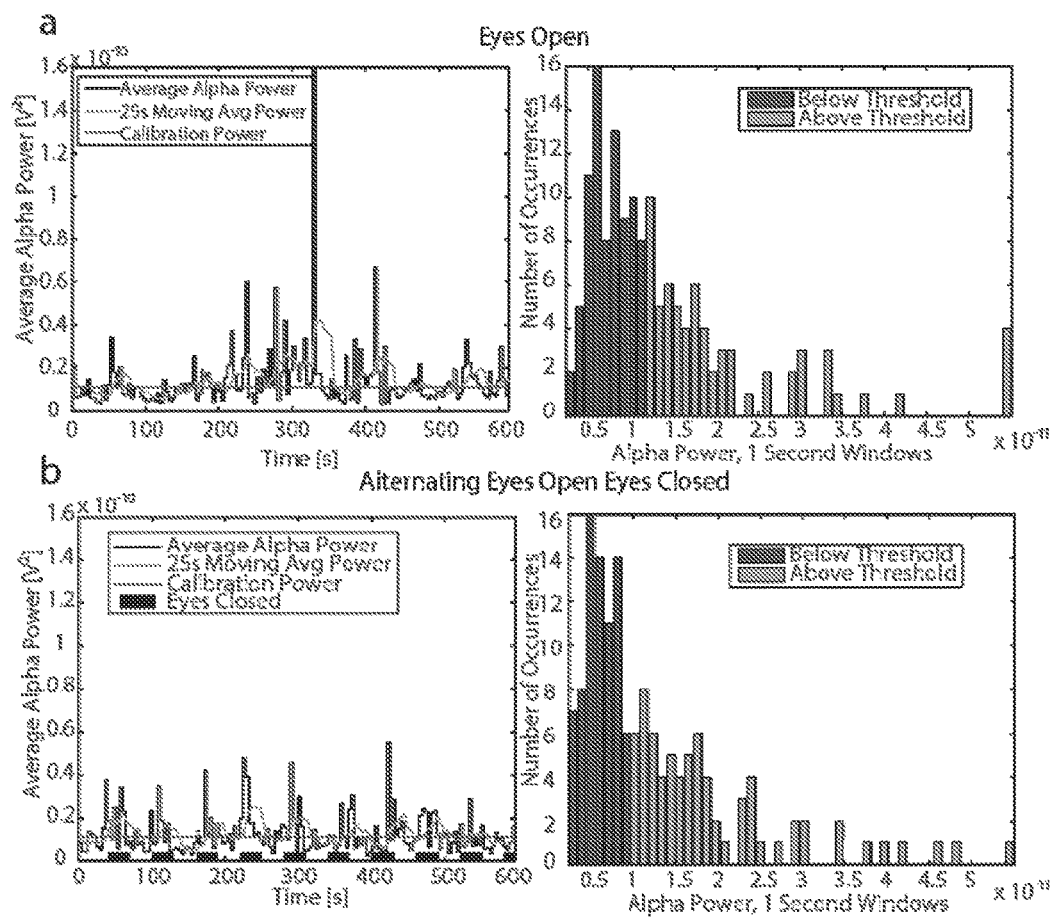
FIGS. 2A-2B are graphs showing endogenous alpha power at O2 with no stimulation applied. Brain activity was recorded for 10 minutes after the subject was prompted to relax while sitting still with eyes open. (A). The subject was then asked to relax, and was instructed to open and close their eyes every 30 s. (B). Left: Average alpha power (black) for each 4 s window as well as the moving average (light grey) and calibration-window threshold (dark grey). Right: Distribution of average alpha power with values below and above calibration-window threshold in dark grey and light grey, respectively, Endogenous alpha power present during eyes closed epochs was significantly higher than a power present during eyes open epochs (ratio of EC$\alpha$ to EO$\alpha$=1.4416, p=0.001).
Figure 3:
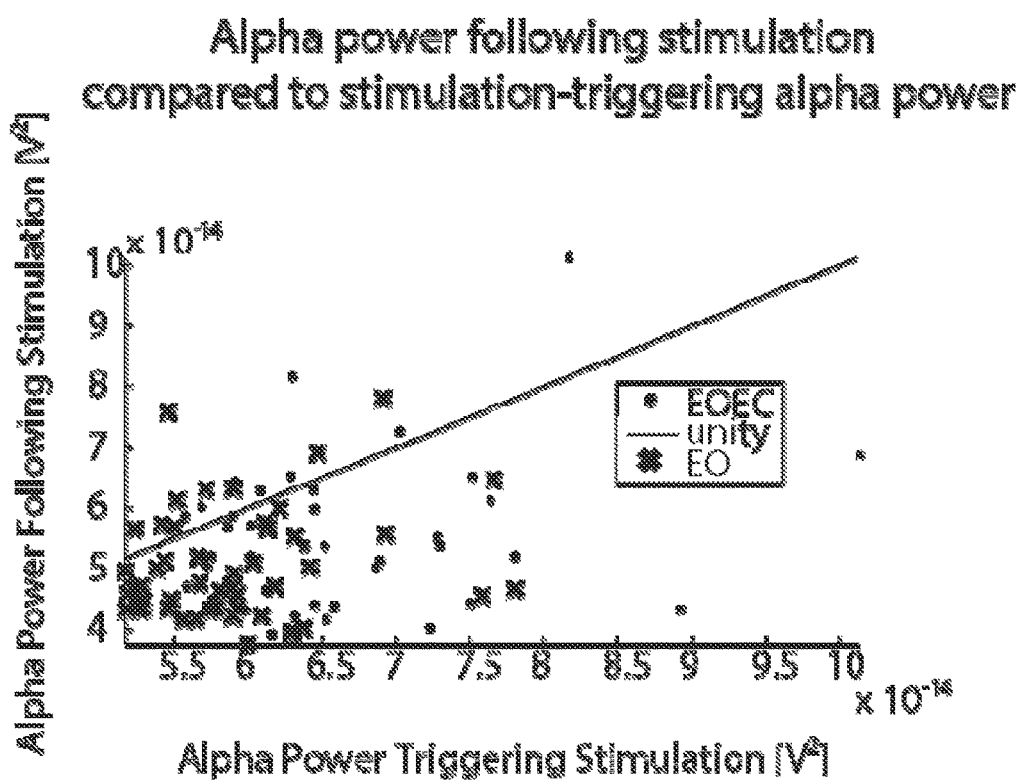
FIG. 3 is a graph comparing stimulation-triggering alpha power to alpha power immediately following stimulation. FB tACS suppressed alpha power in the immediately following window. Median ratio of post-stimulation alpha to pre-stimulation alpha for combined FB EO and FB EOEC=0.83, p<0.001.
Figure 4:
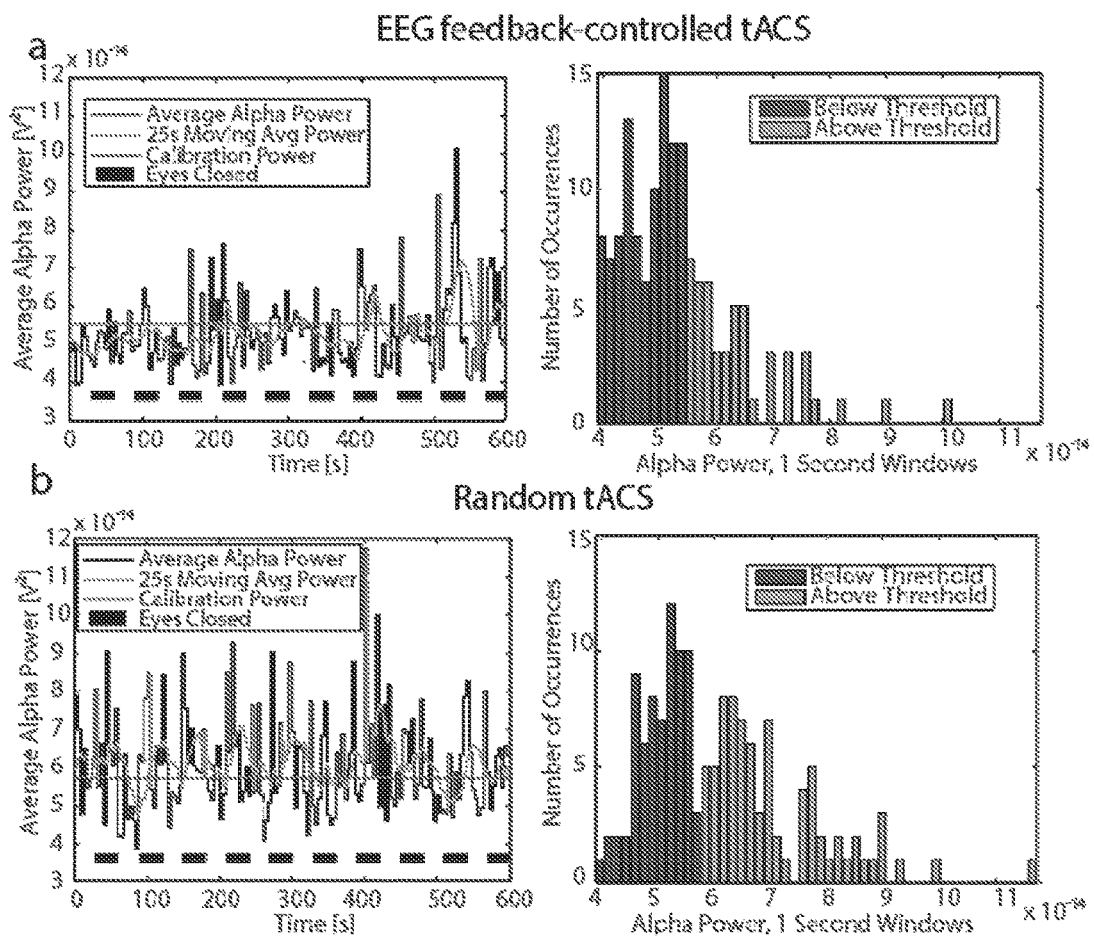
FIGS. 4A-4B are graphs showing endogenous alpha power at O2 during 40 Hz tACS for EOEC. (A) FB tACS almost completely suppressed alpha power in a targeted way (Ratio EC$\alpha$ to EO$\alpha$=1.03, p=0.041). (B) Dose-matched RA tACS also suppressed alpha power (normalized RA-No Stim=−0.31, p=0.0183), but was less effective than FB tACS (normalized FB$\alpha$−RA$\alpha$=−0.10, p=0.0145).
Figure 5:
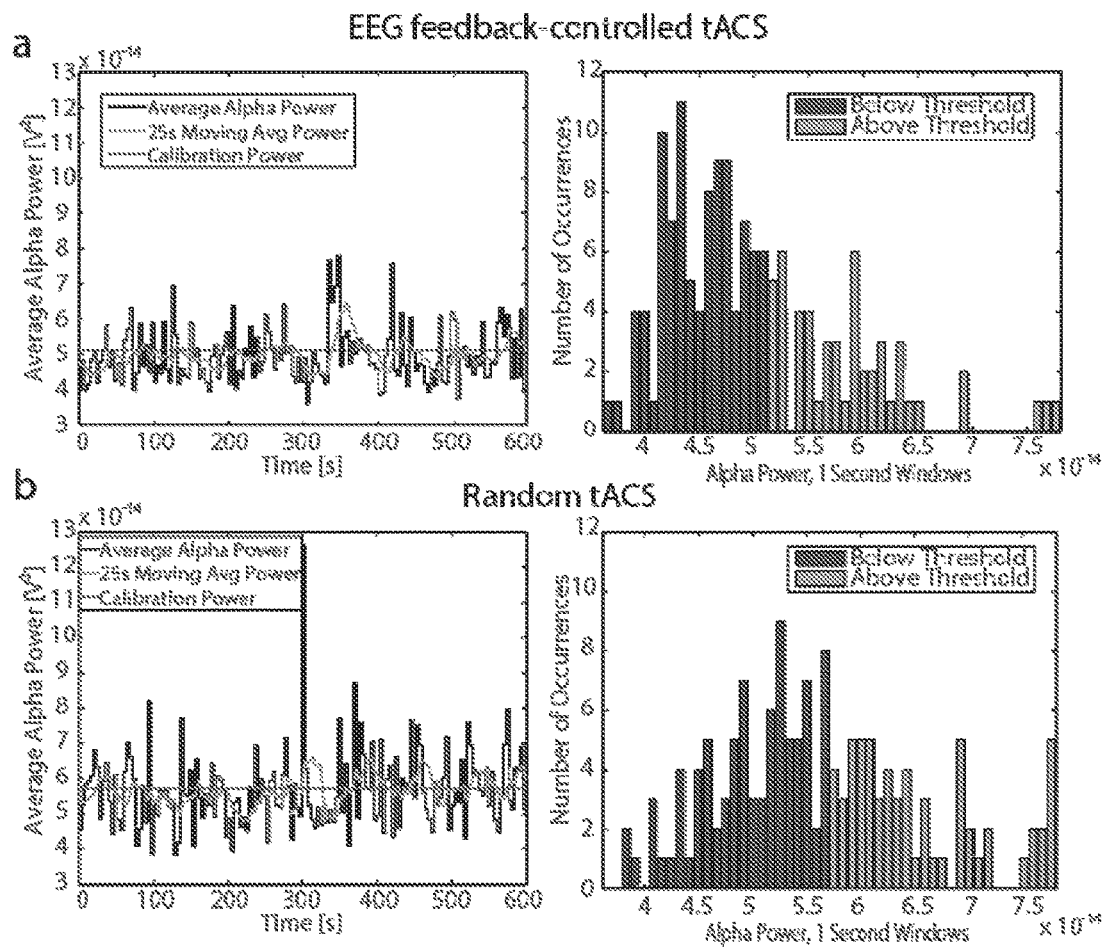
FIGS. 5A-5B are graphs showing the endogenous alpha power at O2 during 40 Hz tACS for EO. (A) FB tACS suppressed alpha power. (B) Dose-matched RA tACS did not suppress alpha power. FB tACS resulted in a lower median normalized alpha power than RA tACS (normalized FB$\alpha$−RA$\alpha$=−0.03, p=0.0004).

We first attached 10 mm gold-plated EEG electrodes to the international 10-20 system sites O2, A1, and A2 in healthy human subjects. We report here pilot data that was collected from two subjects (FIG. 2 is from one subject and FIGS. 3-5 are from the other subject). Then, the stimulation electrodes were placed at Cz and slightly superior to O2. A recent modeling study predicted strong, localized current densities in occipitoparietal regions for a very similar configuration. Neuling et al., FRONT PSYCHIATRY 3:83 (2012). Subjects completed four 12 minute recordings. Each recording started with a 2 minute calibration period. For the first 60 s, the subjects were asked to relax, be still, and keep their eyes open. For the next 60 s, the subjects were asked to relax, be still, and close their eyes. The threshold for stimulation was calculated from this 2 minute period. After calibration, for the first recording, the subjects were asked to relax, sit still, and keep their eyes open (EO). The subjects received FB tACS for this recording. For the second recording, the subjects were asked to open and close their eyes when told (alternating "eyes open" and "eyes closed" every 30 s, EOEC). The subjects also received FB tACS for this recording. The last two recordings were the same as the first two, except that the subjects received dose-matched randomly-administered 40 Hz tACS (RA tACS). During these recordings, the subjects were stimulated as many times as they were during the corresponding FB EO/EOEC recording, but at random. In a separate session, both EO and EOEC were recorded with no stimulator attached to determine the endogenous a activity (FIG. 2). All procedures were approved by the Institutional Review Board (IRB) of the University of North Carolina at Chapel Hill (IRB #12-0022).

D. Data Analysis

Offline data processing was performed with custom MAT-LAB scripts (MathWorks, Natick, Mass.). The alpha power values were normalized by dividing by the stimulation threshold. We used non-parametric tests (Wilcoxon rank sum test, Wilcoxon signed rank test) to establish statistical significance ($p<0.05$).

II. Results

A. Alpha Power Significantly Varied by State

We first characterized the presence of alpha oscillations as a function of whether the eyes were open or closed. We found that alpha power spontaneously fluctuated with eyes open and that opening and closing eyes induced switches between low- and high-power alpha states (FIG. 2A: alpha power during 10 min EO recording; FIG. 2B: alpha power during a 10 min EOEC recording). Both EO and EOEC exhibited substantial variability in alpha power over time. During the EOEC paradigm, these fluctuations were time-locked to the opening and closing of the eyes; the EC intervals had greater median alpha power than the EO intervals of the EOEC recording ($EC\alpha=1.1597\times10-11 V2$, $EO\alpha=0.8045\times10-11$ V2, ratio of $EC\alpha$ to $EO\alpha=1.4416$, $p=0.001$). This median 44% increase in alpha power confirmed the known state-dependence of the alpha oscillation in human visual cortex.

B. FB tACS Suppressed Alpha-Power Fluctuations

We found that our feedback brain stimulation system successfully suppressed alpha power (FIG. 3) as well as state transitions caused by opening and closing the eyes. While the ratio of alpha power during EC and EO was still greater than one (ratio $EC\alpha$ to $EO\alpha=1.0255$, $p=0.041$, FIG. 4), feedback brain stimulation almost completely suppressed the pronounced fluctuations caused by opening and closing the eyes (the ratio of normalized FB-No Stim=−0.42, $p=0.0011$, FIG. 2 and FIG. 4).

In order to establish that the same amount of stimulation applied at random did not have the same efficacy in controlling alpha state dynamics, we applied RA tACS. The ratio $EC\alpha$ to $EO\alpha$ for RA tACS showed that there was more alpha power during eyes closed epochs (ratio $EC\alpha$ to $EO\alpha=1.13$, $p=0.0058$) and that this was also less than the ratio found when no tACS is administered (normalized RA—No Stim=−0.31, $p=0.0183$). However, the ratio $EC\alpha$ to $EO\alpha$ for FB tACS is smaller than ratio $EC\alpha$ to $EO\alpha$ for RA tACS (normalized $FB\alpha-RA\alpha=-0.10$, $p=0.0145$). Therefore, these pilot results demonstrate that feedback brain stimulation is more effective than feedforward stimulation at controlling oscillatory dynamics in the alpha band in visual cortex.

We next examined the efficacy of our feedback control scheme in absence of experimentally-induced state transitions by applying it to subjects that had their eyes open during the entire recording session. We found that in this case FB tACS suppressed normalized alpha power (normalized $FB\alpha=0.9360$, $p=0.0016$) but that RA tACS did not (normalized $RA\alpha=0.9618$, $p=0.1241$, normalized $FB\alpha-RA\alpha=-0.03$, $p=0.0004$, FIG. 5). This suggests that FB tACS can also control more subtle fluctuations of an individual cortical state.

III. Discussion

We here present pilot data on the successful use of a novel non-invasive brain stimulation paradigm that combined tACS and EEG to control state dynamics in human cortex. The increase in alpha oscillations in occipital EEG leads with eyes closed is a well-known phenomenon. Recent work has pointed to brain activity with pronounced alpha oscillations as an important cortical state that alters overall excitability and decouples cortex from sensory input. Lopes da Silva et al, Intl. J. Psychophysiol. 26(1-3):237 (1997); Hanslmayr et al., NEUROIMAGE 37(4):1465 (2007); Palva and Palva, TRENDS IN NEUROSCI. 30(4):150 (2007); Romei et al., J. NEUROSCI. 30(25):8692 (2010); Toscani et al., EXP. BRAIN RES. 207(3-4):213 (2010). Therefore, achieving effective control of alpha oscillations may become a clinically relevant tool for the treatment of a broad range of disorders with cognitive symptoms of altered attentional and sensory processing such as schizophrenia, autism, and attention-deficit disorder.

IV. Conclusion

We here introduce a novel non-invasive feedback brain stimulation paradigm that may (1) open up a new avenue of therapeutic interventions in neuropsychiatric disorders associated with altered state transitions and (2) be used as a tool to investigate the cognitive and behavioral roles of cortical state dynamics. Being able to control biological state variables with feedback control has a track record of enabling ground-breaking discoveries in biology such as the work by Cole, Hodgkin and Huxley (Cole, ANN. REV. NEUROSCI. 5:305 (1982); Hodgkin and Huxley, J. PHYSIOL.-LONDON 117(4):500 (1952)) on the ionic basis of action potential firing by use of the voltage clamp for feedback control of the membrane voltage.

EXAMPLE 2

1. Introduction

Creativity, the ability to produce novel and useful work, is one of the most extraordinary capabilities of the human mind (Sawyer, R. K. (2011). *Explaining creativity: The science of human innovation*: Oxford University Press). Yet, the neural basis of creativity remains poorly understood (Dietrich et al., Psychol. Bull. 136(5), 822-848 (2010)). At the level of macroscopic brain dynamics measured with electroencephalography (EEG), oscillatory activity in the alpha frequency band (8-12 Hz) correlates with creative ideation (Fink et a, Neurosci. Biobehav. Rev. 44C, 111-123 (2014)). In particular, creative idea generation was associated with increased oscillation power in the alpha band in prefrontal and parietal cortical areas (Fink et al., Methods 42(1), 68-76 (2007); Jauk et al., Int. J. Psychophysiol. 84(2), 219-225 (2012)). Also, enhanced alpha power was more pronounced in highly creative people, for more original ideas, and during demanding creative tasks (Fink et al., Neurosci. Biobehav. Rev. 44C, 111-123 (2014)). In further support of the importance of alpha oscillations, creativity-enhancing, behavioral interventions were associated with increased alpha recruitment, especially at frontal brain sites (Fink et al., Eur. J. Neurosci. 23(8), 2241-2246 (2006); Fink et al., Int. J. Psychophysiol. 82(3), 233-239 (2011)). Despite this convergence of evidence of an association between alpha oscillations and creativity, it has remained unknown whether alpha activity is causally involved in creative ideation since previous studies of cognitive enhancement by brain stimulation have focused on targeting specific brain areas and not network dynamics (Luft et al., *Front. Syst. Neurosci.* 8, 132 (2014)). Transcranial alternating current stimulation (tACS) is a non-invasive brain stimulation modality that applies weak, oscillating electric currents to the scalp to entrain endogenous cortical oscillations at the applied frequency (Herrmann et al., Front. Hum. *Neurosci.* 7, 279 (2013); Schmidt et al., *Brain Stimul.* S1935-861X (14), 262-269 (2014)). TACS has recently provided causal evidence for oscillations in specific frequency bands mediating memory consolidation, motor control, sensory processing, and fluid intelligence (Frohlich, *Dialogues Clin. Neurosci.* 16(1), 93 (2014); Herrmann et al., *Front. Hum. Neurosci.* 7, 279 (2013); Santarnecchi et al., *Curr. Biol.* 23(15), 1449-1453 (2013)). Alpha oscillations are likely generated and modulated by thalamo-cortical and intracortical circuits (Bollimunta et al., *J. Neurosci.* 31(13), 4935-4943 (2011); Hindriks et al., *Neuroimage* 70, 150-163 (2013)) and are therefore susceptible to cortical brain stimulation. Indeed, recent advances in simultaneous EEG and tACS have demonstrated that stimulation in the alpha frequency band selectively enhanced alpha oscillations during and briefly after stimulation (Helfrich et al., *Curr. Biol.* 24(3), 333-339 (2014); Zaehle et al., *PLoS One* 5(11), e13766 (2010)). We here used bifrontal tACS in the alpha frequency range (10 Hz-tACS) to determine if alpha oscillations play a causal role in creativity.

2. Materials and Methods 2.1 Participants

Twenty healthy, right-handed participants (5 males, 15 females) aged 19-30 years (20.9±2.7 years; Mean±SD) were recruited from the University of North Carolina at Chapel Hill (UNC) community and signed written consent prior to participation. This study was approved by the UNC IRB. Exclusion criteria were a history of neurologic or psychiatric illness, family history of psychopathology, chronic diseases, current use of psychoactive agents or other medications, brain implants/devices, history of brain surgery, and pregnancy.

2.2. Study Procedure

Figure 6:
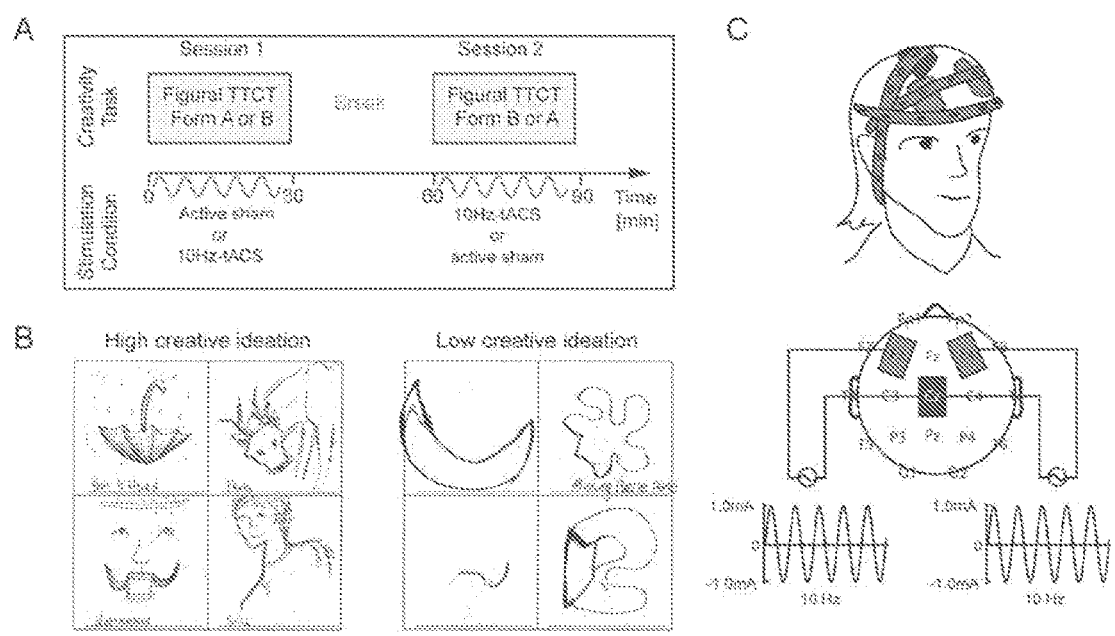
FIGS. 6A-6C show the study design, creativity task, and tACS paradigm. (A) Each participant had two experimental sessions during the same day. 10 Hz-tACS (verum condition) was applied during one of the two sessions (for the duration of the creativity task) and an active sham condition was applied in the other. Stimulation condition and test forms (A or B) of the Torrance Test of Creative Thinking (TTCT) were applied in a randomized and balanced cross-over design during the two sessions. (B) Sample responses of the TTCT picture completion task performed by two participants with different creativity levels. Participants had to use incomplete predefined forms (black), form a new picture, and make up a title for each drawing as original and unique as possible (e.g. "nutcracker" in sample response). Left: Sample response from participant with Creativity Index of 138 (high creative ideation). Right: Participant with Creativity Index of 98 (low creative ideation). (C) Stimulation electrodes were positioned bilaterally over the frontal cortex (centered on EEG electrode locations F3 and F4) with a common electrode over the apex (Cz). Each electrode pair (F3-Cz, F4-Cz) was controlled by a separate stimulation channel that both applied a synchronized 10 Hz sine-wave stimulation waveform with zero phase offset. This configuration allowed for synchronized stimulation of both frontal lobes.

A randomized, crossover design was applied in this study; participants were blinded to the stimulation condition and independent scoring of the creativity assay was done by a third party unaware of the study design. Participants attended a single session consisting of the two parallel forms of the creativity tests (Torrance Test of Creative Thinking, TTCT) during which participants received transcranial Alternating Current Stimulation (tACS). The two tests were separated by a 30 minutes break to minimize contamination of the second session with outlasting effects of the stimulation during the first session (FIG. 6). During one of the 2 sessions, 10 Hz-tACS for 30 minutes (verum condition) was administered for the entire duration of the TTCT. In the other session, 10 Hz-tACS for 5 minutes (active sham condition) was applied. After completing the first test, participants were asked to wait patiently for 30 minutes. Magazines were provided for the participant to read while they waited in between tests. After 30 minutes, participants were given the other form of the TTCT and received either verum or sham stimulation. All iterations of form type, stimulation type, and session order were randomly balanced, and each participant received both verum and sham stimulation. After each test, participants were asked whether or not they believe they received stimulation.

2.3 Torrance Test of Creative Thinking (TTCT)—Figural Task

The TTCT is the most widely used and well-known measure of creativity (Baer, J. (1993). *Creativity and divergent thinking: A task-specific approach*. Hillsdale, N.J.: Lawrence Erlbaum Associates; Kim, *Creativity Res. J.* 18(1), 3-14 (2006)). It was developed to measure divergent thinking, which is a central aspect of creativity. We used the figural version of the task that comes with the two parallel forms A and B (Torrance, E. P. (1998). *The Torrance test of creative thinking norms—technical manual figural (streamlined) forms A & B*. Bensenville, Ill.: Scholastic Testing Service, Inc.). Both forms are composed of three activities: (1) Picture construction requires the participant to complete a given shape (e.g. jelly bean shaped figure) and draw a picture that uses this predefined shape as an integral part of it (2) In picture completion the participants use 10 different incomplete figures to construct and name a new object (3) Repeated figures of lines and circles requires the participants to make new objects from 30 circles or lines and add titles to them (Kim, *Creativity Res. J.* 18(1), 3-14 (2006); Torrance, E. P., & Ball, O. E. (1984). *The Torrance Test of Creative Thinking Streamlined (revised) manual, Figural A and B*. Bensenville, Ill.: Scholastic testing Service, Inc.). Ten minutes are allocated per activity such that the test is completed in 30 minutes (Torrance, E. P. (1998). *The Torrance test of creative thinking norms-technical manual figural (streamlined) forms A & B*. Bensenville, Ill.: Scholastic Testing Service, Inc.). To define the creative potential of the participant, standard scores of five subscales are determined according to the TTCT-norms technical manual (Torrance, E. P. (1998). *The Torrance test of creative thinking norms—technical manual figural (streamlined) forms A & B*. Bensenville, Ill.: Scholastic Testing Service, Inc.) and averaged. The five subscales are Fluency (number of relevant ideas), Originality (number of statistically infrequent data), Elaboration (number of added ideas), Abstractness of Titles (degree beyond labeling), and Resistance to Premature Closures (degree of psychological openness) (Kim, *Creativity Res. J.* 18(1), 3-14 (2006); Torrance, E. P., & Ball, O. E. (1984). *The Torrance Test of Creative Thinking Streamlined (revised) manual, Figural A and B*. Bensenville, Ill.: Scholastic testing Service, Inc.). To determine the final Creativity Index score, 13 criterion-referenced measures (creative strengths, e.g. richness of imaginary) are added to the creative potential scoring (Torrance, E. P., & Ball, O. E. (1984). *The Torrance Test of Creative Thinking Streamlined (revised) manual, Figural A and B*. Bensenville, Ill.: Scholastic testing Service, Inc.). We investigated the effect of 10 Hz-tACS stimulation on overall Creativity Index and all five subscales. Instructions for the task were administered according to the provided manual (Torrance, E. P. (1998). *The Torrance test of creative thinking norms—technical manual figural (streamlined) forms A & B*. Bensenville, Ill.: Scholastic Testing Service, Inc.). Scoring of all the tasks was conducted by an external company (Scholastic Testing Service, STS, Inc., Bensenville, Ill.) that is an expert center in scoring the Torrance tasks and was not informed about the aim or the design of the study (all test booklets were given a random 5-digit identifier). Thus, the evaluation of the task performance was done in an objective and unbiased way, blinded to all experimental factors. Once the scores were returned, the study was unblinded and the national percentiles and standard scores for each participant were adjusted based on participant age using tables provided by STS.

2.4. Transcranial Alternating Current Stimulation (tACS)

Participants were fitted with three rubber stimulation electrodes in saline-moistened sponge envelopes (5×7 cm; NeuroConn Ltd., Ilmenau, Germany). All tACS electrodes were secured to the scalp with rubber head straps. The scalp was first measured in the 10-20 system to mark the locations of the apex of the head (Cz) and the prefrontal cortex (F3 and F4, bilaterally). Two electrodes were placed at F3 and F4, while the third electrode was placed at Cz. Current was passed through the scalp at the three electrode sites using two NeuroConn DC-Stimulator Plus devices (NeuroConn Ltd., Ilmenau, Germany). The electrode at Cz was common between the two stimulators while one stimulator was connected to the electrode at F3 and the other stimulator was connected to the electrode at F4. The two devices were synchronized by external command signals and the presence of constant zero degree phase offset was verified by control measures before stimulation. This configuration allowed for synchronized stimulation of the two frontal hemispheres. The impedance for each current path was kept below 10 k$\Omega$. The sham condition employed a 5 minute, 2 mA peak-to-peak 10 Hz sine wave flanked by 10 second linear envelope ramps in and out for a total duration of 5 minutes and 20 seconds. The verum stimulation employed the same stimulation signal with the one difference that stimulation lasted 30 instead of 5 minutes.

2.5 Statistics

Custom-written scripts in R (R Foundation for Statistical Computing, Vienna, Austria) and SPSS software version 21.0 (IBM, Armonk, N.Y.) were used for the analysis. Libraries used in R included lme4 (Bates et al., (2014). lme4: Linear mixed-effects models using Eigen and S4. R package version 1.1-6. Retrieved from CRAN.R-projectorg/package=lme4) and pbkrtest (Halekoh et al., (in press). A Kenward-Roger approximation and parametric bootstrap methods for tests in linear mixed models—the R package pbkrtest. *J. Statistical Software*.). We performed a linear mixed model analysis of the relationship between Creativity Index derived from the Torrance task and stimulation condition. We entered stimulation condition (sham and verum), session (session 1 and 2) and form (A and B) as fixed factors and participants as a random factor into the model. We used the Kenward-Roger approximation to perform F-tests and to estimate p-values for each factor and their interaction in the mixed model (Halekoh et al., (in press). A Kenward-Roger approximation and parametric bootstrap methods for tests in linear mixed models—the R package pbkrtest. *J. Statistical Software*.). Thereafter, we investigated whether the stimulation condition effect on the Creativity Index was specific to certain subscales of the Creativity Index. We performed a linear mixed model including all the standardized values of the 5 subscales (pooled data), entered stimulation condition (sham or verum) and subscale type (Fluency, Originality, Elaboration, Abstractness of Titles, Resistance to Premature Closures) as fixed factors, and participants as a random factor into the model. F- and p-values were again estimated using the Kenward-Roger approximation (Halekoh et al., (in press). A Kenward-Roger approximation and parametric bootstrap methods for tests in linear mixed models—the R package pbkrtest. *J. Statistical Software*.). Visual inspection of the residual plots of both linear models did not reveal any obvious deviations from normality or homoscedasticity. An exact McNemar's test determined whether there was a statistically significant difference in the proportion of participants perceiving transcranial stimulation between the stimulation conditions. Significance levels were set to $p<0.05$.

3. Results

Participants were successfully blinded to the condition; the number of participants that subjectively reported to perceive tACS stimulation was not significantly different between the stimulation conditions (*Verum*: 18 out of 19; Sham: 14 out of 19, McNemar exact p>0.2). One participant was excluded from the analysis because of the creativity test score during one session that was in the lowest national percentile and clearly deviant from the mean (Creativity Index=50<mean −3*SD).

Figure 7:
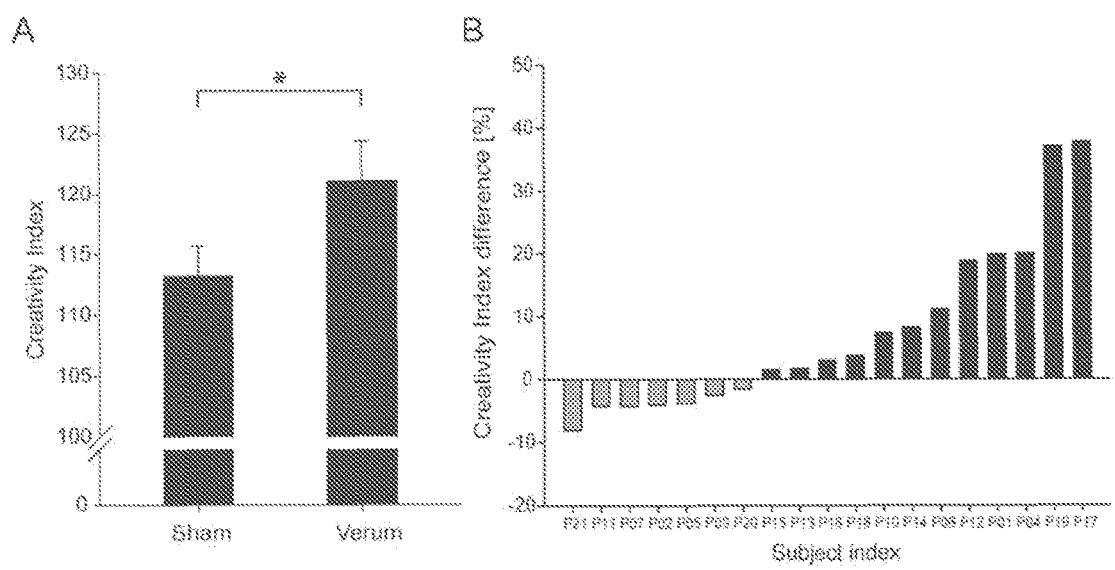
FIGS. 7A-7B show that 10 Hz-tACS increases creative thinking. (A) Creativity Index score, a summary measure of creative potential and strengths, for the verum (10-Hz tACS) and sham stimulation condition (mean+s.e.m). Significance of higher Creativity Index for 10 Hz-tACS compared to sham was determined by linear mixed model analysis (F1, 16=5.14, p=0.036 for factor condition, indicated by star). (B) Individual percentage change in Creativity Index relative to sham (no change to sham denoted as 0%). Participants were sorted according to their tACS related relative improvement in creative thinking. Black bars illustrate participants with a relative increase (N=12) and grey bars participants with a relative decrease (N=7).
Figure 8:
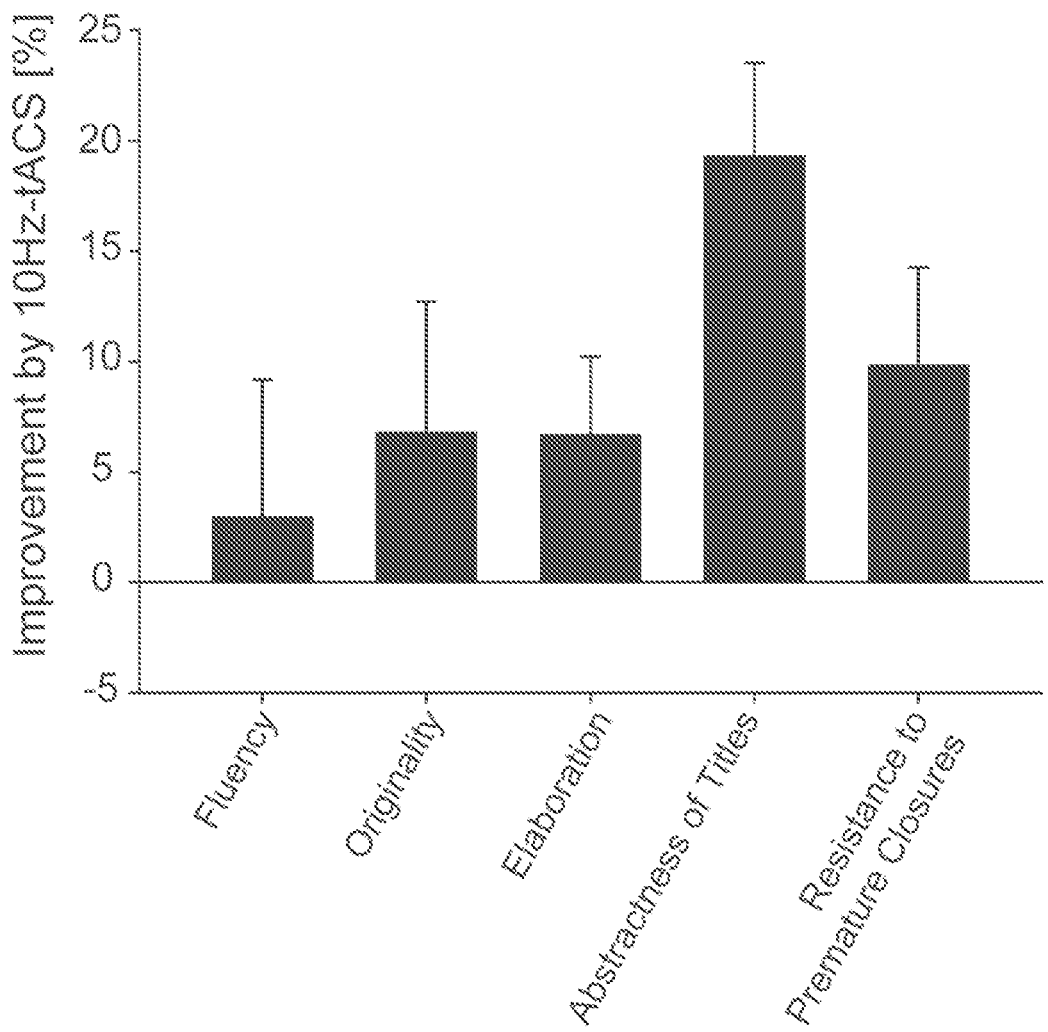
FIG. 8 shows 10 Hz-tACS effects on individual creativity subscales. 10 Hz-tACS increased creative thinking across all subscales (mean+s.e.m. percentage change in TTCT subscales relative to sham). Linear mixed model analysis revealed overall significant stimulation condition effect including all subscales ($F_{1,166}=15.43$, $p<0.001$) but no significant interaction between subscales and stimulation condition ($F_{4,162}=1.58$, $p=0.18$).

Creativity Index, the overall measure of creative potential and strengths derived from the TTCT (Torrance, E. P. (1998). *The Torrance test of creative thinking norms—technical manual figural (streamlined) forms A & B*. Bensenville, Ill.: Scholastic Testing Service, Inc.), was significantly higher under 10 Hz-tACS stimulation compared to active sham (mean percentage difference 7.45%±3.11% s.e.m.; $F_{1,16}=5.14$, p=0.036; FIG. 7A). Twelve out of 19 participants showed a pronounced increase in creative thinking during 10 Hz-tACS compared to sham (FIG. 7B). Linear mixed model analysis further revealed that there was no effect of session ($F_{1,16}=0.57$, p=0.46), form ($F_{1,16}=1.18$, p=0.29), or any interaction between the included factors (all p>0.25). The Creativity Index in the TTCT is comprised of five subscales (Fluency, Originality, Elaboration, Abstract of Titles, and Resistance to Premature Closures) that all showed on average a 10 Hz-tACS related improvement (FIG. 8). We next tested whether the stimulation effect was different for these specific subscales of the Creativity Index; we included the standard scores of all five subscales into a linear mixed model and tested whether there was an interaction between the factor subscale and stimulation condition. No significant interaction was found ($F_{4,162}=1.58$, p=0.18) indicating that the stimulation condition effect was not related to specific subscales. In agreement with the significant enhancing effect of 10 Hz-tACS on the Creativity Index, we again found a strong stimulation condition effect in this analysis ($F_{1,166}=15.43$, p<0.001).

4. Discussion

Our results demonstrate that enhancement of bilateral frontal alpha activity during a standardized divergent thinking test results in enhanced creativity. This finding represents the first direct evidence for a causal role of alpha oscillations in creative ideation.

Why do alpha oscillations mediate creativity? Alpha activity, especially in frontal brain areas, may reflect high-demand internal processing (e.g. imagination) and top-down, inhibitory control processes (e.g inhibition of task-irrelevant processes), which is an important requirement for creative ideation (Benedek et al., *Neuropsychologia* 49(12), 3505-3511 (2011); Klimesch et al., *Brain Res. Rev.* 53(1), 63-88 (2007)). In particular, creative ideation or divergent thinking requires the generation of internal ideas with an inhibitory cognitive control mechanism that prevents disruption of this internal process by incoming salient but irrelevant stimuli (Benedek et al., *Pers. Individ. Dif.* 53-334 (4), 480-485 (2012); Fink et al., *Neurosci. Biobehav. Rev.* 44C, 111-123 (2014)). Thus, increased alpha activity elicited by frontal 10 Hz-tACS might improve top-down control of internal demands and thereby allow better creative ideation.

We simultaneously applied in phase alpha frequency stimulation to both frontal areas in both hemispheres. Besides increased alpha power, our stimulation paradigm may have also enhanced phase synchronization between frontal regions that could also account for improved creativity. Synchronization of oscillatory phases between different brain regions, especially in the theta and gamma frequency range, fosters working memory and long-term memory by facilitating neural communication and by supporting neural plasticity (Fell et al., *Nat. Rev. Neurosci.* 12(2), 105-118 (2011)). However, it is unknown if and how creativity relates to phase-synchronization or coherence in the alpha range between left and right frontal regions.

Top-down inhibitory control processes are not only involved in creative thinking but are also strongly associated with other cognitive tasks (e.g. working memory (Gazzaley et al., *Trends Cogn. Sci.* 16(2), 129-135 (2012); Sauseng et al., *Hum. Brain Mapp.* 26(2), 148-155 (2005)). Given our findings on the effect of 10 Hz-tACS on creativity, further examination of the causal role of alpha activity in those inhibitory processes in cortical areas seems warranted. Of note, deficits in inhibitory top-down processes increase with age (Gazzaley et al., *Nat. Neurosci.* 8(10), 1298-1300 (2005)) and are present in psychiatric and neurological disorders such as schizophrenia (Koh et al., *Schizophr. Res.* 126(1-3), 36-42 (2011)), and Huntington's and Parkinson's disease (Henderson et al., *Mov. Disord.* 26(10), 1893-1899 (2011)). Modulations of alpha oscillations using repetitive transcranial magnetic stimulation (rTMS) have previously been successful in manipulating higher-order cognitive processes as visual attention (Romei et al., *J. Neurosci.* 30(25), 8692-8697 (2010)) and mental rotation (Klimesch et al., *Eur. J. Neurosci.* 17(5), 1129-1133 (2003)). These processes also likely rely on inhibitory top-down control processes (Mechelli et al., *Cereb. Cortex* 14(11), 1256-1265 (2004); Zanto et al., *Nat. Neurosci.* 14(5), 656-661 (2011). Alpha activity enhancement through tACS might therefore open the gates to novel neurotherapeutic approaches based on non-invasive brain stimulation that targets deficits in higher-order cognitive function such as creativity and fluid intelligence, and top-down control processes in particular.

The foregoing is illustrative of the present invention, and is not to be construed as limiting thereof. The invention is defined by the following claims, with equivalents of the claims to be included herein.

That which is claimed:

1. A method of modulating cortical activity in a subject, comprising:
    detecting cortical oscillations and/or coherence between cortical oscillations in the subject via an electrocardiogram, a pupilometer and/or a functional near-infrared spectrometer; and
    passing an oscillating electric current through the skull of the subject responsive to the cortical oscillations and/or coherence detected.

2. A method of modulating cortical activity in a subject, comprising:
    detecting cortical oscillations and/or coherence between cortical oscillations in the subject by identifying one or more changes in the subject's pupil diameter, the subject's heart rate and/or the regularity of the subject's heart beat; and
    passing an oscillating electric current through the skull of the subject responsive to the cortical oscillations and/or coherence detected.

3. A method of modulating cortical activity in a subject, comprising:
    detecting cortical oscillations and/or coherence between cortical oscillations in the subject; and
    passing an oscillating electric current through the skull of the subject, wherein the oscillating electric current is responsive to:
    an increase in the average magnitude of the cortical oscillations over a defined period of time,
    a decrease in the average magnitude of the cortical oscillations over a defined period of time,
    an increase in the variance of the magnitude of the cortical oscillations over a defined period of time,
    a decrease in the variance of the magnitude of the cortical oscillations over a defined period of time,
    an increase in the integral of the magnitude of the cortical oscillations,
    a decrease in the integral of the magnitude of the cortical oscillations,
    an increase in the average integral of the magnitude of the cortical oscillations,
    a decrease in the average integral of the magnitude of the cortical oscillations,
    an increase in the variance of the integral of the magnitude of the cortical oscillations,
    a decrease in the variance of the integral of the magnitude of the cortical oscillations,
    an increase in the temporal derivative of the magnitude of the cortical oscillations,
    a decrease in the temporal derivative of the magnitude of the cortical oscillations,
    an increase in the average temporal derivative of the magnitude of the cortical oscillations,
    a decrease in the average temporal derivative of the magnitude of the cortical oscillations,
    an increase in the variance of the temporal derivative of the magnitude of the cortical oscillations; and
    a decrease in the variance of the temporal derivative of the magnitude of the cortical oscillations.

4. A method of modulating cortical activity in a subject, comprising:
    detecting cortical oscillations and/or coherence between cortical oscillations in the subject; and
    passing an oscillating electric current through the skull of the subject responsive to the cortical oscillations and/or coherence detected, wherein the oscillating electric current has a magnitude sufficient to prevent the cortical oscillations from exceeding an upper threshold or falling below a lower threshold.

* * * * *